(12) United States Patent
Fu et al.

(10) Patent No.: US 6,897,023 B2
(45) Date of Patent: May 24, 2005

(54) METHOD FOR DETERMINING RELATIVE ABUNDANCE OF NUCLEIC ACID SEQUENCES

(75) Inventors: Rongdian Fu, El Cerrito, CA (US); Sydney Brenner, La Jolla, CA (US); Glenn Albrecht, Redwood City, CA (US)

(73) Assignees: The Molecular Sciences Institute, Inc., Berkeley, CA (US); Solexa, Inc., Hayward, CA (US)

(*) Notice: Subject to any disclaimer, the term of this patent is extended or adjusted under 35 U.S.C. 154(b) by 0 days.

(21) Appl. No.: 09/967,238

(22) Filed: Sep. 27, 2001

(65) Prior Publication Data

US 2003/0027157 A1 Feb. 6, 2003

Related U.S. Application Data

(60) Provisional application No. 60/235,940, filed on Sep. 27, 2000.

(51) Int. Cl.[7] .................. C12Q 1/68; C12P 19/34; C07H 21/02; C07H 21/04; C07H 21/00
(52) U.S. Cl. ............... 435/6; 435/91.1; 536/23.1; 536/24.3; 536/24.33; 536/25.3; 536/25.32
(58) Field of Search ............... 435/6, 91.1, 183; 436/94; 536/23.1, 24.3, 24.33, 25.3, 25.32

(56) References Cited

U.S. PATENT DOCUMENTS

| | | | |
|---|---|---|---|
| 5,616,465 A | * | 4/1997 | Lucas et al. ............ 435/6 |
| 5,858,656 A | | 1/1999 | Deugau et al. |
| 6,027,894 A | | 2/2000 | Sapolsky et al. |
| 6,511,802 B1 | * | 1/2003 | Albrecht et al. ............ 435/6 |

FOREIGN PATENT DOCUMENTS

| WO | WO 99/35293 | 7/1999 |
|---|---|---|
| WO | WO 00/09756 | 2/2000 |

OTHER PUBLICATIONS

Jiang, H. et al., "RaSH, a rapid subtraction hybridization approach for identifying and cloning differentially expressed genes", Proceedings of the National Academy of Sciences, vol. 97, No. 23, pp. 12684–12689, Nov. 2000.

* cited by examiner

Primary Examiner—Kenneth R. Horlick
(74) Attorney, Agent, or Firm—LeeAnn Gorthey; Perkins Coie LLP

(57) ABSTRACT

Disclosed are methods for identifying nucleic acid sequences which are of different abundances in different nucleic acid source populations, e.g. differentially expressed genes or genomic variations among individuals or populations of individuals. In one embodiment, probes derived from the source nucleic acid populations are derivatized with a terminal sample ID (SID) sequence characteristic of that population. Upon competitive hybridization of the probes to a reference or index nucleic acid library containing all the sequences in the populations being compared, the SID tags remain single stranded, and those from the different sources are then annealed to one another. Unhybridized (remainder) SID sequences are then quantified. By labeling such remainder SID sequences with a fluorescent dye, FACS sorting of beads containing the hybridized probes can be carried out. The signal ratio upon which such sorting is based is enhanced compared to competitive hybridization using labeled probes without SID sequences.

20 Claims, 18 Drawing Sheets

SEQUENCE LISTING

```
<160> NUMBER OF SEQ ID NOS: 24

<210> SEQ ID NO 1
<211> LENGTH: 73
<212> TYPE: DNA
<213> ORGANISM: Artificial Sequence
<220> FEATURE:
<223> OTHER INFORMATION: exemplary tag library
<221> NAME/KEY: misc_feature
<222> LOCATION: (1)...(73)
<223> OTHER INFORMATION: n = A,T,C or G
```

```
<400> SEQUENCE: 1
agaattcggg ccttaattaa dddddddddd dddddddddd dddddddddd ddgggcccgc    60
ataagtcttc nnn                                                      73

<210> SEQ ID NO 2
<211> LENGTH: 18
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(18)
<223> OTHER INFORMATION: n = A,T,C or G

<400> SEQUENCE: 2
atcactngga tccnnnnn                                                 18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agaattcggg ccttaattaa                                               20

<210> SEQ ID NO 4
<211> LENGTH: 25
<212> TYPE: DNA
<213> ORGANISM: Artificial Sequence
<220> FEATURE:
<223> OTHER INFORMATION: adaptor
<221> NAME/KEY: misc_feature
<222> LOCATION: (1)...(1)
<223> OTHER INFORMATION: 5' nucleotide modified to include phosphate
      group

<400> SEQUENCE: 4
atcgagagaa gagcgtgcac aggaa                                         25

<210> SEQ ID NO 5
<211> LENGTH: 22
<212> TYPE: DNA
<213> ORGANISM: Artificial Sequence
<220> FEATURE:
<223> OTHER INFORMATION: adaptor

<400> SEQUENCE: 5
ttcctgtgca cgctcttctc tc                                            22

<210> SEQ ID NO 6
<211> LENGTH: 19
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(1)
<223> OTHER INFORMATION: 5' nucleotide modified to include biotin

<400> SEQUENCE: 6
ttcctgtgca cgctcttct                                                19

<210> SEQ ID NO 7
<211> LENGTH: 25
```

```
<212> TYPE: DNA
<213> ORGANISM: Artificial Sequence
<220> FEATURE:
<223> OTHER INFORMATION: adaptor
<221> NAME/KEY: misc_feature
<222> LOCATION: (1)...(1)
<223> OTHER INFORMATION: 5' nucleotide modified to include phosphate
      group

<400> SEQUENCE: 7
atcctcagaa gagcgtgcac tccga                                              25

<210> SEQ ID NO 8
<211> LENGTH: 22
<212> TYPE: DNA
<213> ORGANISM: Artificial Sequence
<220> FEATURE:
<223> OTHER INFORMATION: adaptor

<400> SEQUENCE: 8
tcggagtgca cgctcttctg ag                                                 22

<210> SEQ ID NO 9
<211> LENGTH: 19
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(1)
<223> OTHER INFORMATION: 5' nucleotide modified to include biotin

<400> SEQUENCE: 9
tcggagtgca cgctcttct                                                     19

<210> SEQ ID NO 10
<211> LENGTH: 40
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(1)
<223> OTHER INFORMATION: 5' nucleotide modified to include biotin

<400> SEQUENCE: 10
gacatgccty cattgagacg attcttttttt tttttttttv                             40

<210> SEQ ID NO 11
<211> LENGTH: 45
<212> TYPE: DNA
<213> ORGANISM: Artificial Sequence
<220> FEATURE:
<223> OTHER INFORMATION: cDNA primer construct
<221> NAME/KEY: misc_feature
<222> LOCATION: (1)...(1)
<223> OTHER INFORMATION: 5' nucleotide modified to include biotin
<221> NAME/KEY: misc_feature
<222> LOCATION: (1)...(45)
<223> OTHER INFORMATION: n = A,T,C or G

<400> SEQUENCE: 11
gacatgctgc attgagacga ttctttttttt tttttttttt tvnnn                       45

<210> SEQ ID NO 12
<211> LENGTH: 37
<212> TYPE: DNA
<213> ORGANISM: Artificial Sequence
<220> FEATURE:
```

<223> OTHER INFORMATION: cDNA primer construct
<221> NAME/KEY: misc_feature
<222> LOCATION: (1)...(37)
<223> OTHER INFORMATION: n = A,T,C or G

<400> SEQUENCE: 12
gcattgagac gattctttt tttttttttt tttvnnn         37

<210> SEQ ID NO 13
<211> LENGTH: 36
<212> TYPE: DNA
<213> ORGANISM: Artificial Sequence
<220> FEATURE:
<223> OTHER INFORMATION: cDNA primer construct
<221> NAME/KEY: misc_feature
<222> LOCATION: (1)...(36)
<223> OTHER INFORMATION: n = A,T,C or G

<400> SEQUENCE: 13
nnnbaaaaaa aaaaaaaaaa aagaatcgtc tcannn         36

<210> SEQ ID NO 14
<211> LENGTH: 61
<212> TYPE: DNA
<213> ORGANISM: Artificial Sequence
<220> FEATURE:
<223> OTHER INFORMATION: cloning vector

<400> SEQUENCE: 14
ttaattaagg adddddddd dddddddddd dddddddddd dddgggcccg cataagtctt    60
c                                                                  61

<210> SEQ ID NO 15
<211> LENGTH: 28
<212> TYPE: DNA
<213> ORGANISM: Artificial Sequence
<220> FEATURE:
<223> OTHER INFORMATION: synthetic spacer
<221> NAME/KEY: misc_feature
<222> LOCATION: (28)...(28)
<223> OTHER INFORMATION: 3' nucleotide attached to a bead

<400> SEQUENCE: 15
tccttaatta actggtctca ctgtcgca                  28

<210> SEQ ID NO 16
<211> LENGTH: 18
<212> TYPE: DNA
<213> ORGANISM: Artificial Sequence
<220> FEATURE:
<223> OTHER INFORMATION: adaptor
<221> NAME/KEY: misc_feature
<222> LOCATION: (1)...(1)
<223> OTHER INFORMATION: 5' nucleotide modified to include phosphate
      group
<221> NAME/KEY: misc_feature
<222> LOCATION: (18)...(18)
<223> OTHER INFORMATION: 3' nucleotide modified to include fluorescein
      dye

<400> SEQUENCE: 16
gatcacgagc tgccagtc                             18

<210> SEQ ID NO 17
<211> LENGTH: 14
<212> TYPE: DNA
<213> ORGANISM: Artificial Sequence
<220> FEATURE:

```
<223> OTHER INFORMATION: adaptor

<400> SEQUENCE: 17
gactggcagc tcgt                                                    14

<210> SEQ ID NO 18
<211> LENGTH: 22
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(1)
<223> OTHER INFORMATION: 5' nucleotide modified to include biotin

<400> SEQUENCE: 18
agtgaattcg ggccttaatt aa                                           22

<210> SEQ ID NO 19
<211> LENGTH: 32
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(1)
<223> OTHER INFORMATION: 5' nucleotide modified to include fluorescein
      dye

<400> SEQUENCE: 19
gtacccgcgg ccgcggtcga ctctagagga tc                                32

<210> SEQ ID NO 20
<211> LENGTH: 19
<212> TYPE: DNA
<213> ORGANISM: Artificial Sequence
<220> FEATURE:
<223> OTHER INFORMATION: probe SID decoder

<400> SEQUENCE: 20
agaagagcgt gcacaggaa                                               19

<210> SEQ ID NO 21
<211> LENGTH: 22
<212> TYPE: DNA
<213> ORGANISM: Artificial Sequence
<220> FEATURE:
<223> OTHER INFORMATION: probe SID decoder
<221> NAME/KEY: misc_feature
<222> LOCATION: (1)...(1)
<223> OTHER INFORMATION: 5' nucleotide modified to include two PEG
      chains and a Cy5 dye

<400> SEQUENCE: 21
ttcctgtgca cgctcttctc tc                                           22

<210> SEQ ID NO 22
<211> LENGTH: 19
<212> TYPE: DNA
<213> ORGANISM: Artificial Sequence
<220> FEATURE:
<223> OTHER INFORMATION: probe SID decoder

<400> SEQUENCE: 22
agaagagcgt gcactccga                                               19

<210> SEQ ID NO 23
```

-continued

```
<211> LENGTH: 22
<212> TYPE: DNA
<213> ORGANISM: Artificial Sequence
<220> FEATURE:
<223> OTHER INFORMATION: probe SID decoder
<221> NAME/KEY: misc_feature
<222> LOCATION: (1)...(1)
<223> OTHER INFORMATION: 5' nucleotide modified to include two PEG
      chains and a fluorescein dye

<400> SEQUENCE: 23
tcggagtgca cgctcttctg ag                                              22

<210> SEQ ID NO 24
<211> LENGTH: 16
<212> TYPE: DNA
<213> ORGANISM: Artificial Sequence
<220> FEATURE:
<223> OTHER INFORMATION: 3' end of exemplary tag sequence
<221> NAME/KEY: misc_feature
<222> LOCATION: (1)...(16)
<223> OTHER INFORMATION: n = A,T,C or G

<400> SEQUENCE: 24
nnnggatccg agtgat                                                     16
```

METHOD FOR DETERMINING RELATIVE ABUNDANCE OF NUCLEIC ACID SEQUENCES

This application claims priority to U.S. provisional application Ser. No. 60/235,940, filed Sep. 27, 2000, which is hereby incorporated by reference in its entirety.

FIELD OF THE INVENTION

The invention relates generally to methods for identifying nucleic acid sequences which are of different abundances in different sources, e.g. differentially expressed genes or genomic variations among individuals. More particularly, it relates to a method of competitively hybridizing cDNA or genomic DNA probe libraries with reference DNA sequences cloned on solid phase supports, and to methods of sorting such solid phase supports by fluorescence-activated flow sorting (FACS) with high resolution.

BACKGROUND

The desire to decode the human genome and to understand the genetic basis of disease and a host of other physiological states associated with differential gene expression has been a key driving force in the development of improved methods for analyzing and sequencing DNA. However, the large number of expressed genes in the human genome makes it difficult to track changes in expression patterns by direct sequence analysis. More commonly, expression patterns are analyzed by lower resolution techniques, such as differential display, indexing, subtraction hybridization, or one of the numerous DNA fingerprinting techniques (e.g. Lingo et al,. Science 257: 967–971, 1992); McClelland et al., U.S. Pat. No. 5,437,975; Unrau et al., Gene 145: 163–169, 1994); Sagerstrom et al., Ann. Rev. Biochem. 66: 751–783, 1997). For techniques that result in the isolation of a subset of DNA sequences, sequencing of randomly selected clones is typically carried out using conventional Sanger sequencing; thus, the scale of the analysis is limited.

Recently, several higher resolution techniques have been reported that attempt to provide direct sequence information for analyzing patterns of gene expression on a large scale: Schena et al., Science 270: 467–469 (1995), and DeRisi et al, Science 278: 680–686 (1997), report the hybridization of mRNAs to a collection of cDNAs arrayed on a glass slide; Velculescu et al., Science 270: 484–486 (1995), report the excision and concatenation of short segments of sequence adjacent to type IIs restriction sites from members of a cDNA library, followed by Sanger sequencing of the concatenated segments to give a profile of sequences in the library; and Wodicka et al., Nature Biotechnology 15: 1359–1367 (1997), report genome-wide expression monitoring of yeast under different growth conditions using high density oligonucleotide arrays containing hybridization sites for each of the more than 6000 genes of the organism. While these techniques represent tremendous progress in expression analysis, they still have drawbacks which limit their widespread application to many expression monitoring problems. For example, in both the techniques of Schena and Wodicka, the sequences being monitored must be known beforehand, and in the case of Wodicka, preferably the entire complement of an organism's genes must be known. In the technique of Schena, there are significant problems in constructing arrays containing a substantial portion, e.g. ten thousand, or more, of genes whose expression may be relevant, as cDNAs of each gene are separately prepared and applied to an array, and currently available arrays are typically not re-usable, leading to standardization and quality control issues when multiple measurements over time are desired. In the technique of Velculescu, even though the sequencing burden is reduced, abundant non-differentially expressed genes are sequenced repeatedly, as with any random sequencing approach, at the expense of obtaining expression information on differentially regulated genes. In addition, it is not clear from the reported data whether the technique is capable of providing sample sizes sufficiently large to permit the reliable expression profiling of genes that are expressed very low levels (e.g. Kollner et al., Genomics, 23: 185–191, 1994).

Co-owned U.S. Pat. No. 6,265,163 provides a method of massive parallel analysis of all or a substantial fraction of expressed genes, allowing selection of differentially expressed genes from non-differentially expressed genes, without requiring prior knowledge of the differentially expressed sequences being monitored. More generally, the method allows detection and isolation of differentially represented nucleic acids from any two nucleic acid populations.

In accordance with this method, also described in Brenner et al., PNAS 97:1665–70 (2000), differently labeled populations of DNAs from sources to be compared are competitively hybridized with reference DNA cloned on solid phase supports, e.g. microparticles, to provide a differential expression library which, in the preferred embodiment, is manipulated by fluorescence-activated cell sorting (FACS). Monitoring the relative signal intensity of the different fluorescent labels on the microparticles permitted quantitative analysis of relative expression levels between the different sources. An illustration of the process is given in Example 4 herein. Populations of microparticles having relative signal intensities of interest were isolated by FACS, and the attached DNAs identified by sequencing, such as with massively parallel signature sequencing (MPSS), or with conventional DNA sequencing protocols. Such methods also can be used for identifying differentially represented variations in genomic DNA, e.g. SNP's, deletions, or duplications.

In FACS sorting as applied to these methods, the original ratio of probes in the compared sources is reflected by the ratio of probes hybridized to the target DNA beads and, hence, the ratio of the two fluorescence signals of the beads. Beads with different ratios of fluorescence signals are detected and are sorted from each other according to preset gate(s). See, for example, FIGS. 1A–1B.

For a model system of two equally sized populations of beads, a bead population having hybridized probes at a molar ratio as low as 3:1 could be sorted from a bead population with a 1:1 molar ratio of two probes, using the methods described in U.S. Pat. No. 6,265,163. However, limitations in FACS sorting prevented accurate sorting of beads having lower ratios of the two probes from the much greater population of beads having DNAs equally represented in the two populations. See, for example, FIGS. 5A–E in U.S. Pat. No. 6,265,163, reproduced as FIGS. 11A–e herein. Methods of distinguishing and sorting beads having probes at these lower ratios were desired. Accordingly, the present invention provides methods of improving the resolution of such sorting.

SUMMARY OF THE INVENTION

In one aspect, the invention provide a method for determining the relative abundance of a nucleic acid sequence among at least two nucleic acid populations. The method comprises the following steps:

A first probe, derived from a first nucleic acid population, having a sequence which is complementary to a selected sequence and a terminal first sample ED (SID) sequence, and a second probe, derived from a second nucleic acid population, having a sequence which is complementary to the selected sequence and a terminal second sample ID (SID) sequence, wherein the first and second probes are present in relative amounts proportional to the abundance of the nucleic acid sequence in the respective populations, are contacted with a reference library which comprises multiple copies of the selected nucleic acid sequence. Upon such contacting, the first and second probes competitively hybridize with the selected sequence in the reference library, such that the probes are present in duplexes in relative amounts proportional to the abundance of the nucleic acid sequence in the respective populations, and the SID sequences are present as single stranded extensions on the duplexes. The first SID sequences on the duplexes and the second SID sequences on the duplexes are then hybridized with each other in a 1:1 ratio, and the presence of unhybridized SID sequences is detected, as an indication of the relative amounts of hybridized first probe and hybridized second probe.

The first and second SID sequences are preferably complementary and thus hybridize with each other directly. Alternatively, the first and second SID sequences may hybridize with each other through an intermediate molecule comprising sequences complementary to the first and second SID sequences; in this case, the method further comprises, concurrent with or following the contacting of the probes to the reference library, contacting the intermediate molecule with the reference library and probes. In the preferred embodiment, a plurality (or library) of probes derived from the first population and a plurality (or library) of probes derived from the second population are contacted with the reference library, and the reference library comprises multiple copies of the sequences present in the first and second populations, such that different sequences within the library are attached to spatially distinct solid phase supports in clonal subpopulations. The spatially distinct solid phase supports may be, for example, separate regions of a planar support, or discrete microparticles.

In another preferred embodiment, detecting the unhybridized (or "remainder") SID sequences comprises attaching to each the unhybridized SID sequence a labeled decoder moiety. Preferably, a first light-generating label is present on first decoder moieties selectively attachable to unhybridized first SID sequences, and a second, distinguishable light generating label is present on second decoder moieties selectively attachable to unhybridized second SID sequences. Such selective attachment is typically achieved by using for each decoder moiety an oligonucleotide having a terminal oligonucleotide sequence that is complementary to either the first or the second SID sequence. The label is preferably a fluorescent molecule, e.g. a fluorescent dye, and a decoder moiety may comprise multiple fluorescent molecules.

In further embodiments, the first and second probes, a known fraction of the first and second probes, are further labeled with the first and second light-generating labels, respectively.

The method also includes, where the spatially distinct solid phase supports are microparticles, the step of sorting the microparticles by FACS according to the ratio of fluorescent signals generated by the fluorescent labels on each microparticle. Microparticles having a value of the ratio of fluorescent signals within one or more selected ranges of values may be separated, and the nucleotide sequence of a portion of the nucleic acid sequence on one or more of the microparticles determined, by various sequencing methods.

The method can be used, for example, analysis of differentially regulated or expressed genes, wherein the populations are cDNA libraries derived from expressed genes of each of a plurality of sources selected from different cells, tissues, or individuals; and the reference DNA library is derived from genes expressed in the plurality of different sources. The method can also be used in analysis of genetic variations among individuals or populations of individuals, wherein the populations are genomic DNA libraries derived from different individuals or populations of individuals, and the reference DNA library is derived from pooled genomic DNA of such individuals or populations of individuals.

In a related aspect, the invention provides a method for sorting a population of nucleic acid sequences in accordance with their relative abundance between at least two nucleic acid populations, the method comprising:

(a) contacting with a reference library which comprises the nucleic acid sequences present in the nucleic acid populations, such that different sequences within the library are attached to spatially distinct solid phase supports in clonal subpopulations:

a plurality of probes derived from the first population, each probe having a sequence which is complementary to a reference library sequence, and a terminal first sample ID (SID) sequence, and a plurality of probes derived from the second population, each probe having a sequence which is complementary to a reference library sequence, and a terminal second sample ID (SID) sequence, wherein the first and second probes having a given sequence, exclusive of the SID sequence, are present in relative amounts proportional to the abundance of the sequence in the respective populations, and whereby, upon such contacting, (i) the first and second probes competitively hybridize with complementary sequences in the reference library, such that the probes of a given sequence are present in duplexes in relative amounts proportional to the abundance of that nucleic acid sequence in the respective populations, and the SID sequences are present as single stranded extensions on the duplexes; and (ii) the first SID sequences on the duplexes and the second SID sequences on the duplexes hybridize with each other in a 1:1 ratio;

(b) applying to each unhybridized SID sequence a decoder moiety having a fluorescent label, wherein a first fluorescent label is present on first decoder moieties selectively attachable to unhybridized first SID sequences, and a second, distinguishable fluorescent label is present on second decoder moieties selectively attachable to unhybridized second SID sequences; and (c) sorting the microparticles by FACS according to the ratio of fluorescent signals generated by the fluorescent labels on each microparticle.

Preferably, each decoder moiety includes a terminal oligonucleotide sequence that is complementary to either the first or the second SID sequence. The decoder moieties may comprise multiple fluorescent molecules.

In further related aspects, the invention provides kits containing components for carrying out the methods of the invention. One such kit, for use in determining the relative abundance of nucleic acid sequences among at least two nucleic acid populations, derived from a plurality of sources selected from different cells, different tissues, different individuals, and different populations of individuals, includes the following:

(i) a reference nucleic acid library containing the sequences present in the plurality of different sources, wherein different sequences within the library are attached to separate solid phase supports in clonal subpopulations;

(ii) a first plurality of probes, derived from a nucleic acid library from one of the plurality of sources, each probe having appended a terminal first SID sequence, and (iii) a second plurality of probes, derived from a nucleic acid library from a second of the plurality of sources, each probe having appended a terminal second SID sequence, which is able to hybridize with the first SID sequence.

The kit may also include (iv) a first decoder moiety, selectively attachable to the first SID sequence, having a first light-generating label, and (v) a second decoder moiety, selectively attachable to the second SID sequence, having a second, distinguishable light-generating label. Preferably, each decoder moiety is an oligonucleotide having a terminal sequence complementary to the first or second SID sequence, respectively, and each label comprises a fluorescent molecule, or multiple fluorescent molecules. The first and second pluralities of probes, or known fractions of the first and second pluralities of probes, may also be labeled with the first and second distinguishable light-generating labels, respectively.

Another such kit, for use in preparation of sequence ID (SID) tagged probes, competitive hybridization, and SRQ decoding, for use in the methods of the invention, includes:

(a) two or more SID adaptors for generating SID tagged probes, each the adaptor comprising a double stranded oligonucleotide having, in sequence: (i) a protruding single strand effective for ligation to a DNA restriction fragment, (ii) a sample ID sequence, (ii) a restriction site, and (iv) a primer binding site, wherein cleavage by an enzyme recognizing the restriction site is effective to cleave all but elements (i) and (ii) from the adaptor, and wherein different adaptors have different sample ID sequences which are able to hybridize with each other; and (b) two or more sample ID decoders, selectively attachable to the different sample ID sequences, and having distinguishable light-generating labels.

The kit may also include a reference nucleic acid library containing DNA sequences present in the two or more nucleic acid populations, wherein different sequences within the library are attached to separate solid phase supports, e.g. microparticles, in clonal subpopulations.

These and other objects and features of the invention will become more fully apparent when the following detailed description of the invention is read in conjunction with the accompanying drawings.

DEFINITIONS

Figure 1A:
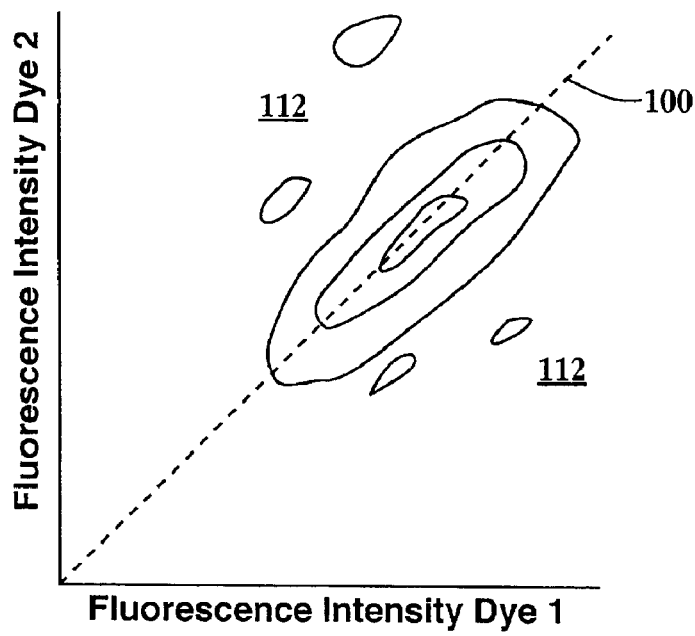
FIGS. 1A and 1B illustrate FACS analysis of microparticles loaded with competitively hybridized DNA strands labeled with two different fluorescent dyes.

The terms below have the following meanings unless indicated otherwise.

"Complement" or "tag complement", as used herein in reference to oligonucleotide tags, refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. When an oligonucleotide is represented by a sequence of letters, such as "ATGCCTG," it will be understood that the nucleotides are in 5'→3' order from left to right, and that "A" denotes deoxyadenosine, "C" denotes deoxycytidine, "G" denotes deoxyguanosine, and "T" denotes thymidine, unless otherwise noted. Usually, oligonucleotides comprise the four natural nucleotides; however, they may also comprise non-natural nucleotide analogs. It is clear to those skilled in the art when oligonucleotides having natural or non-natural nucleotides may be employed; e.g., where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-amninopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, *DNA Replication*, 2nd Ed. (Freeman), San Francisco, 1992. "Analogs", in reference to nucleosides, includes synthetic nucleosides having modified base moieties and/or modified sugar moieties, e.g. as described by Scheit, *Nucleotide Analogs* (John Wiley, New York, 1980); Uhlman and Peyman, *Chemical Reviews* 90: 543–584 (1990), or the like, with the proviso that they are capable of specific hybridization. Such analogs include synthetic nucleosides designed to enhance binding properties, reduce complexity, increase specificity, and the like.

As used herein, "sequence determination" or "determining a nucleotide sequence", in reference to polynucleotides, includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C)-C . . . " and the like.

As used herein, the term "complexity" in reference to a population of polynucleotides refers to the number of different species of polynucleotide present in the population.

As used herein, the term "relative gene expression" or "relative expression", in reference to a gene, refers to the relative abundance of the same gene expression product, usually an mRNA, in different cells or tissue types.

DETAILED DESCRIPTION OF THE INVENTION

I. SID Remainder Quantification Method

The present invention provides a method for determining the relative abundance of nucleic acid sequence(s) in a collection, or library, of such sequences. The invention also provides a method for sorting and/or isolating differentially represented sequences, i.e. sequences having different relative abundances, among different collections of nucleic acids. As described in co-owned U.S. Pat. No. 6,365,163 and in Brenner et al., *PNAS* 97:1665–70 (2000), differently labeled populations of DNAs from sources to be compared can be competitively hybridized with reference DNA cloned on solid phase supports, e.g. microparticles, to provide a differential expression library, which can be manipulated by fluorescence-activated cell sorting (FACS). Monitoring the relative signal intensity of the different fluorescent labels on the microparticles permitted quantitative analysis of expression levels of the two populations relative to each other.

Because, in many cases, microparticles having equal numbers of probe sequences from the two sources greatly outnumber those have unequal numbers, sorting resolution can be critical when separating microbeads bearing the two probes in unequal but low ratios. According to the present invention, sequences having relative abundance ratios as low as 1.2:1, or even lower, can be separated from equally represented sequences (i.e. those having a 1:1 ratio) using the method of the invention.

Figure 2A:
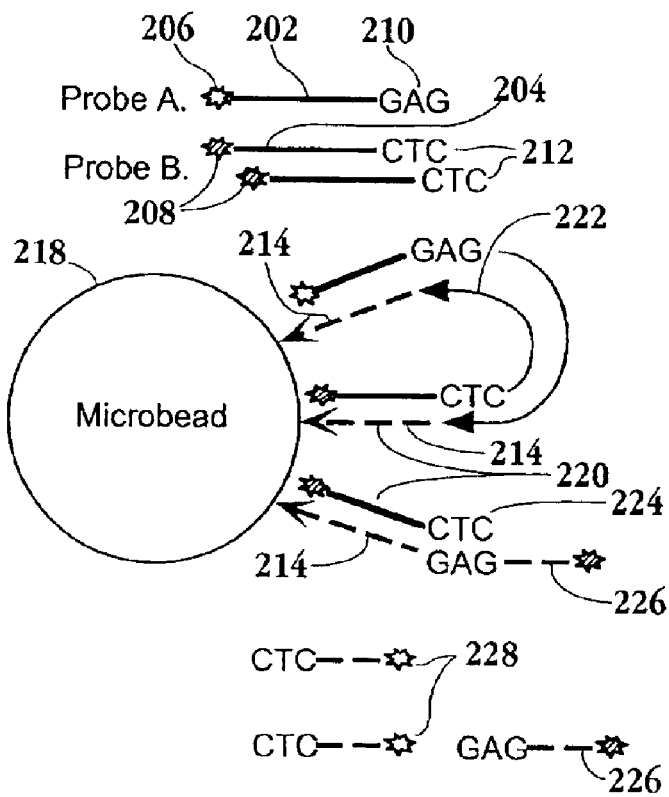
FIG. 2A illustrates enhancement of signal ratios in competitive hybridization assays by SID (or subtraction) remainder quantification (SRQ), in accordance with one embodiment of the invention.
Figure 2B:
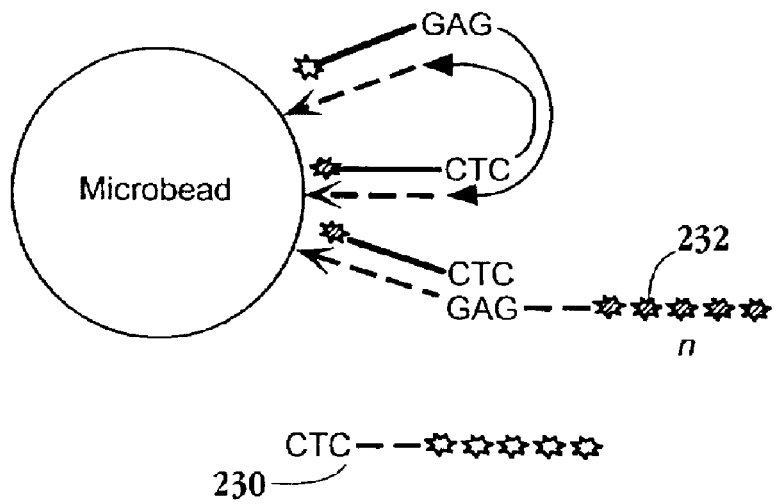
FIG. 2B illustrates the use of multiply labeled decoder molecules for further signal ratio enhancement.

The method, which is illustrated schematically in FIGS. 2A–B, employs DNA probes (202,204) prepared from each sample population (e.g. cDNA or genomic DNA libraries), where each probe is labeled with one of two distinguishable labels (206,208), preferably a fluorescent dye, and contains at a terminus one of two "sample identifier" (SID) sequences (210,212), which are able to hybridize with each other. A corresponding library of target sequence clones (214) is prepared, where each clone is attached to a discrete solid surface, e.g. a collection of microbeads (218) or discrete regions on a solid array. Competitive hybridization of the probes to the microbead library is carried out, whereupon probes of the same sequence from two samples hybridize to their complimentary strands on a given region or bead, forming duplexes (220), but with the SID sequences remaining single stranded. The SIDs are then "titrated" by hybridization/ligation (222) of the two types of SIDs from two samples on the same microbead or region. The "remainder" (unhybridized) SID sequences (224) are quantified, preferably via the use of a pair of SID decoder molecules (226,228), which allows the relative abundance of each sequence to be to determined, as the (enhanced) ratio of two fluorescence intensity signals. As shown in FIGS. 2A–B, a 2:1 intensity ratio, which would have been obtained by simply using labeled probes, is enhanced to 3:1. Use of multiply labeled decoders (230, 232) as shown in FIG. 2B, gives even greater enhancement. The quantification process is referred to herein as SID (or subtraction) remainder quantification, or SRQ, and the SID sequence-tagged probes as SRQ probes. Flow cytometry analysis can be used to identify and sort DNA clones which are differentially represented in the two samples.

The method could also employ, as SID tags, binding pairs other than complementary oligonucleotides; e.g. complementary oligonucleotide analogs, such as PNAs (peptide nucleic acids), biotin/streptavidin, antibody/antigen, or enzyme/substrate. In another embodiment, magnetic particles could be used as labels in place of fluorescent molecules, and the microbeads sorted by MACS (Magnetically Activated Cell Sorting). In this case, sorting could distinguish abundance of label, but not different types of labels, as in FACS. For ease of preparation and other factors, oligonucleotide SID's and decoders and fluorescent labels are preferred.

In one embodiment, the invention provides a method for analyzing for the presence of differentially represented genetic variations in genomic DNA among different individuals. Such variations can include, for example, SNPs (single nucleotide polymorphisms), deletions, and duplications. In another embodiment, the invention provides a method for analyzing relative gene expression in a plurality of cells and/or tissues that are of interest. The plurality usually comprises a pair of cell or tissue types, such as a diseased tissue or cell type and a healthy tissue or cell type, or such as a cell or tissue type being subjected to a stimulus or stress, e.g. a change of nutrients, temperature, or the like, and the corresponding cell or tissue type in an unstressed or unstimulated state. The plurality may also include more than two cell or tissue types, such as would be required in a comparison of expression patterns of the same cell or tissue over time, e.g. liver cells after exposure of an organism to a candidate drug, organ cells of a test animal at different developmental states, and the like. Preferably, the plurality is 2 or 3 cell or tissue types; and more preferably, it is 2 cell or tissue types.

For analysis in accordance with the latter embodiment, messenger RNA (mRNA) is extracted from the cells or tissues of interest using conventional protocols, as disclosed in, for example, Sambrook et al., *Molecular Cloning: A Laboratory Manual*, 2nd Edition (Cold Spring Harbor Laboratory, New York). Preferably, the populations of mRNAs to be compared are converted into populations of labeled cDNAs by reverse transcription in the presence of a labeled nucleoside triphosphate using conventional protocols, e.g. Schena et al., *Science* 270: 467–470 (1995); DeRisi et al., *Science* 278: 680–686 (1997); or the like, prior to hybridization to a reference DNA population.

An important benefit of the methods described herein is that the genes whose expression levels change or are different than those of the other cells or tissues being examined may be analyzed separately from those that are not regulated or otherwise altered in response to whatever stress or condition is being studied. Similarly, DNA fragments which represent genomic variations among individuals may be analyzed separately from those which are equally represented among the individuals.

Another important benefit of the methods described herein is that the identity of the nucleic acids being analyzed, e.g. genomic DNA, cDNA, mRNA, RNA transcript, or the like, need not be known prior to analysis. After relative abundance is determined, nucleic acids of interest may be identified by direct sequencing on the solid phase support, preferably a microparticle, using a number of different sequencing approaches. For identification, only a portion of the DNAs need be sequenced. In many cases, the portion may be as small as nine or ten nucleotides; see e.g. Velculescu et al. (cited above). Entire subpopulations of differentially expressed genes can be sequenced simultaneously using MPSS (massively parallel signature sequencing) or a similar parallel analysis technique. In a preferred embodiment, this is conveniently accomplished by providing the reference DNA population of DNA sequences such that each such sequence is attached to a separate microparticle in a clonal subpopulation. As explained more fully below, clonal subpopulations are preferably formed by so-called "solid phase cloning", as disclosed in Brenner, U.S. Pat. No. 5,604,097 and Brenner et al., PCT Pubn. No. WO 9641011. Briefly, such clonal subpopulations are formed by hybridizing an amplified sample of oligonucleotide tag-DNA conjugates onto one or more solid phase support(s), e.g. separate microparticles, so that individual microparticles, or different regions of a larger support, have attached multiple copies of the same DNA. Such oligonucleotide tags, not to be confused with the sequence identifier (SID) tags of the present method, are described further in Section I below, and in further detail in the above-cited references by Brenner.

The number of copies of a DNA sequence in a clonal subpopulation may vary widely in different embodiments, depending on several factors, including the density of tag complements on the solid phase supports, the size and composition of microparticle used, the duration of hybridization reaction, the complexity of the tag repertoire, the concentration of individual tags, the tag-DNA sample size, the labeling means for generating optical signals, the particle sorting means, signal detection system, and the like. Guidance for making design choices relating to these factors is readily available in the literature on flow cytometry, fluorescence microscopy, molecular biology, hybridization technology, and related disciplines, as represented by the references cited herein.

The number of copies of a DNA in a clonal subpopulation (i.e., the loading on the microparticle) should be sufficient to permit FACS sorting of microparticles, wherein fluorescent signals are generated by one or more fluorescent dye molecules attached to the DNAs attached to the microparticles, as described further below. Typically, this number can be as low as a few thousand, e.g. 3,000–5,000, when a fluorescent molecule such as fluorescein is used, and as low as several hundred, e.g. 800–8000, when a rhodamine dye, such as rhodamine 6G, is used. Preferably, clonal subpopulations consist of at least $10^4$ copies of a cDNA; and most preferably, clonal subpopulations consist of at least $10^5$ copies of a cDNA. When remainder quantification enhanced FACS, as described herein, is employed, the optimal loading, which determines the spacing between molecules on the surface, will also depend on the length of the DNA molecules on the microparticles. In this method, the ends of the DNA molecules must be able to reach each other, so that SID sequences of hybridized probes are able to contact each other. Accordingly, longer DNA molecules can be loaded to a lesser density than shorter DNA molecules. Again, $10^4$–$10^5$ molecules, or more, per particle is generally appropriate.

Labeled DNAs or RNAs from the cells or tissues to be compared are competitively hybridized to the DNA sequences of the reference DNA population using conventional hybridization conditions, e.g. such as disclosed in Schena et al. (cited above); DeRisi et al. (cited above); or Shalon, Ph.D. Thesis entitled "DNA Microarrays," Stanford University (1995). After hybridization, an optical signal is generated by each of the two labeled species of DNAs or RNAs, so that a relative optical signal is determined for each microparticle. Such optical signals are generated and measured in a fluorescence activated cell sorter, or like instrument, which permits the microparticles whose relative optical signal fall within a predetermined range of values to be sorted and accumulated. In accordance with the present invention, as described below, relative optical signals as low as about 1.2/1, and possibly lower, can be detected and sorted.

II. Oligonucleotide Tags for Solid Phase Cloning and Identification

Oligonucleotide "tags" are preferably used to construct reference DNA populations attached to solid phase supports, preferably microparticles, for use in the method of the invention. Such tags (not to be confused with the SID sequence tags of the invention) and methods of their preparation and use are described in detail in PCT Pubn. Nos. WO 9641001 and WO 9612014 and in co-owned U.S. Pat. No. 5,604,097, which are incorporated herein by reference in their entirety. Oligonucleotide tags, when used with their corresponding tag complements, provide a means of enhancing specificity of hybridization for sorting, tracking, or labeling molecules, especially polynucleotides, such as cDNAs or mRNAs derived from expressed genes.

Oligonucleotide tags for sorting may range in length from 12 to 60 nucleotides or basepairs. Preferably, oligonucleotide tags range in length from 18 to 40 nucleotides or basepairs, and more preferably from 25 to 40 nucleotides or basepairs. Preferably, repertoires of single stranded oligonucleotide tags for sorting contain at least 100 members; more preferably, repertoires of such tags contain at least 1000 members; and most preferably, repertoires of such tags contain at least 10,000 members. As used herein in reference to oligonucleotide tags and tag complements, the term "repertoire" means the total number of different oligonucleotide tags or tag complements that are employed for solid phase cloning (sorting) or for identification.

Preferably, tag complements in mixtures, whether synthesized combinatorially or individually, are selected to have similar duplex or triplex stabilities to one another so that perfectly matched hybrids have similar or substantially identical melting temperatures. This permits mismatched tag complements to be more readily distinguished from perfectly matched tag complements in the hybridization steps, e.g. by washing under stringent conditions.

When oligonucleotide tags are used for sorting, as is the case for constructing a reference DNA population, tag complements are preferably attached to solid phase supports. Such tag complements can be synthesized on the surface of the solid phase support, such as a microscopic bead or a specific location on an array of synthesis locations on a single support, such that populations of identical, or substantially identical, sequences are produced in specific regions. Preferably, tag complements are synthesized combinatorially on microparticles, so that each microparticle has attached many copies of the same tag complement. A wide variety of microparticle supports may be used with the invention, including microparticles made of controlled pore glass (CPG), highly cross-linked polystyrene, acrylic copolymers, cellulose, nylon, dextran, latex, polyacrolein, and the like, as known in the art.

Polynucleotides to be sorted, or cloned onto a solid phase support, each have an oligonucleotide tag attached, such that different polynucleotides have different tags. This condition is achieved by employing a repertoire of tags substantially greater than the population of polynucleotides and by taking a sufficiently small sample of tagged polynucleotides from the full ensemble of tagged polynucleotides. After such sampling, when the populations of supports and polynucleotides are mixed under conditions which permit specific hybridization of the oligonucleotide tags with their respective complements, identical polynucleotides sort onto particular beads or regions. The sampled tag-polynucleotide conjugates are preferably amplified, e.g. by polymerase chain reaction, cloning in a plasmid, RNA transcription, or the like, to provide sufficient material for subsequent analysis.

An exemplary tag library for use in sorting is shown below (SEQ ID NO:1).

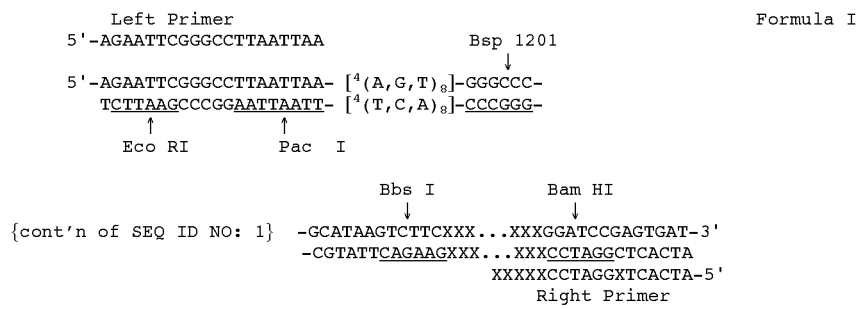

The flanking regions of the oligonucleotide tag may be engineered to contain restriction sites, as exemplified above, for convenient insertion into and excision from cloning vectors. Optionally, the right or left primers (SEQ ID NOs:2 and 3) may be synthesized with a biotin attached (using conventional reagents, e.g. available from Clontech Laboratories, Palo Alto, Calif.) to facilitate purification after amplification and/or cleavage. Preferably, for making tag-fragment conjugates, the above library is inserted into a conventional cloning vector, such as pUC19, or the like. Optionally, the vector containing the tag library may contain a "stuffer" region, "XXX . . . XXX," which facilitates isolation of fragments fully digested with, for example, Bam HI and Bbs I.

Sorting and attachment of populations of DNA sequences in a reference library, e.g. a cDNA or genomic library, to microparticles or to separate regions on a solid phase support is carried out such that each microparticle or region has substantially only one kind of sequence attached; that is, such that the DNA sequences are present in clonal subpopulations. Preferably, at least ninety-five percent of the DNA sequences have unique tags attached. This objective is accomplished by ensuring that substantially all different DNA sequences have different tags attached. This condition, in turn, is brought about by sampling the full ensemble of tag-DNA sequence conjugates for analysis. (It is acceptable that identical DNA sequences have different tags, as it merely results in the same DNA sequence being operated on or analyzed twice.) Such sampling can be carried out either overtly—for example, by taking a small volume from a larger mixture—after the tags have been attached to the DNA sequences; it can be carried out inherently as a secondary effect of the techniques used to process the DNA sequences and tags; or sampling can be carried out both overtly and as an inherent part of processing steps. If a sample of n tag-DNA sequence conjugates are randomly drawn from a reaction mixture, as could be effected by taking a sample volume, the probability of drawing conjugates having the same tag is described by the Poisson distribution, $P(r)=e^{-\lambda}(\lambda)^r/r$, where r is the number of conjugates having the same tag and $\lambda=np$, where p is the probability of a given tag being selected. If $n=10^6$ and $p=1/(1.67\times 10^7)$ (for example, if eight 4-base words as described in Brenner et al. were employed as tags), then $\lambda=0.0149$ and $P(2)=1.13\times10^{-4}$. Thus, a sample of one million molecules gives rise to an expected number of doubles well within the preferred range. Such a sample is readily obtained by serial dilutions of a mixture containing tag-fragment conjugates.

Preferably, DNA sequences are conjugated to oligonucleotide tags by inserting the sequences into a conventional cloning vector carrying a tag library. See, for example, FIG. 3A, discussed further below, where vector (316) contains tag (310). For example, DNA fragments may be constructed having a Bsp 120 I site at their 5' ends and after digestion with Bsp 120 I and another enzyme such as Sau 3A or Dpn II may be directionally inserted into a pUC19 carrying the tags of Formula I to form a tag-DNA library, which includes every possible tag-DNA pairing. A sample is taken from this library for amplification and sorting. Sampling may be accomplished by serial dilutions of the library, or by simply picking plasmid-containing bacterial hosts from colonies. After amplification, the tag-DNA conjugates may be excised from the plasmid.

Figure 3A:
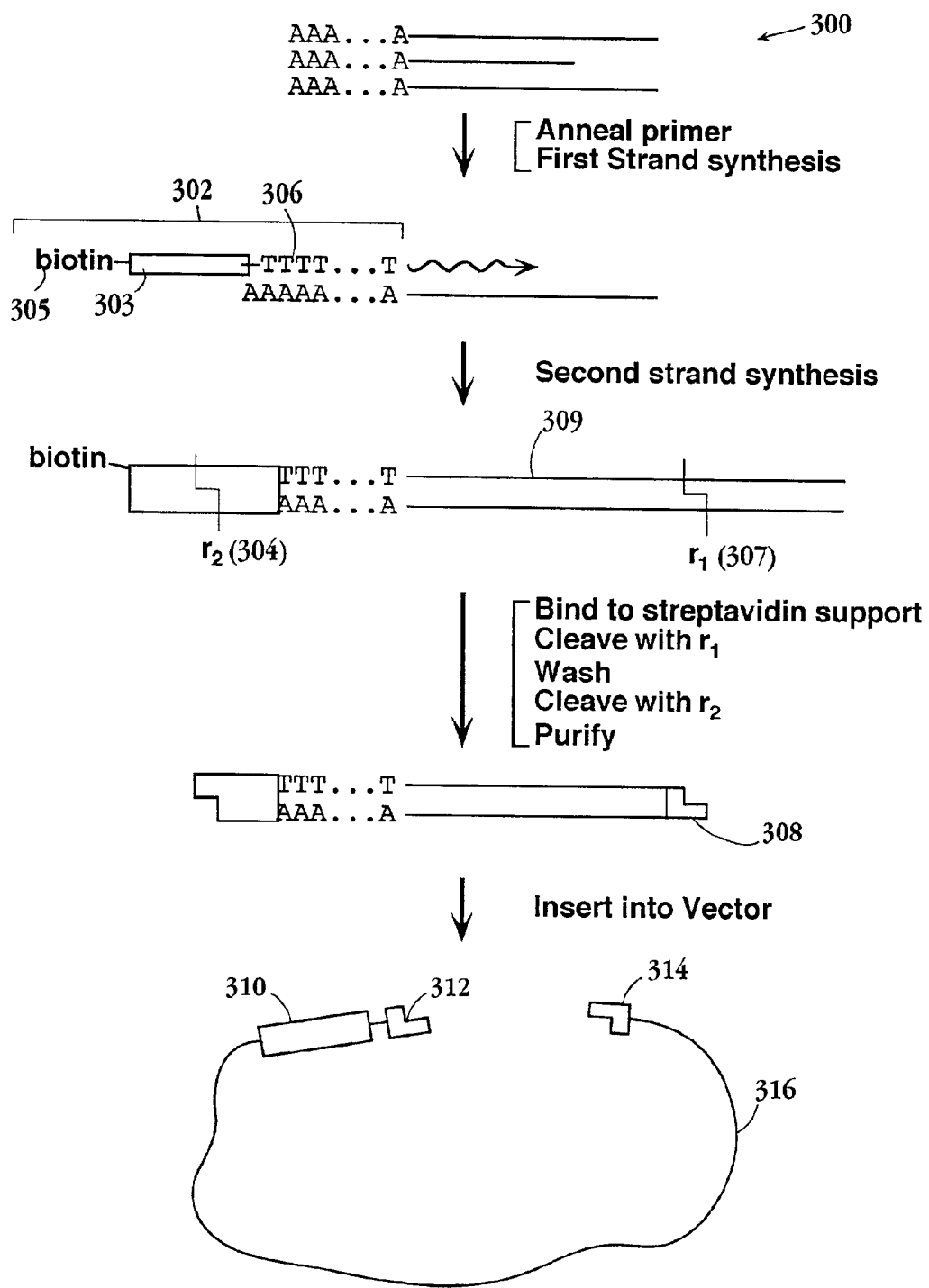
FIG. 3A illustrates a preferred scheme for converting isolated messenger RNA (mRNA) into cDNA and insertion of the cDNA into a tag-containing vector.
Figure 3B:
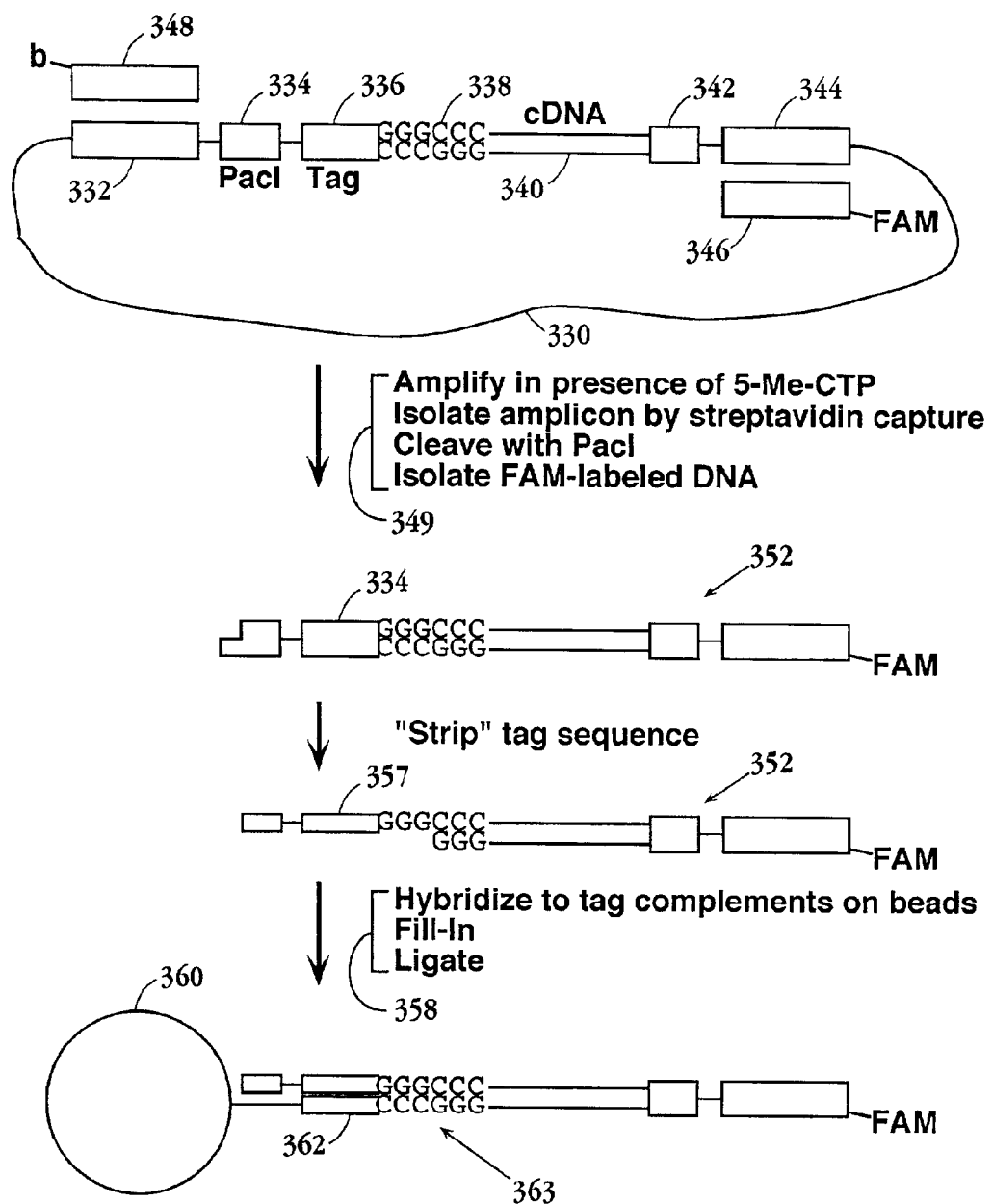
FIG. 3B illustrates a preferred scheme for amplifying tag-DNA conjugates out of a vector and loading the amplified conjugates onto microparticles.

The DNA–tag conjugates are mixed with microparticles containing the tag complements (e.g. as shown in FIG. 3B) under conditions that favor the formation of perfectly matched duplexes between the tags and their complements. There is extensive guidance in the literature for creating these conditions. Exemplary references providing such guidance include Wetmur, *Critical Reviews in Biochemistry and Molecular Biology*, 26: 227–259 (1991); Sambrook et al., *Molecular Cloning: A Laboratory Manual*, 2nd Edition (Cold Spring Harbor Laboratory, New York, 1989); and the like. Preferably, the hybridization conditions are sufficiently stringent so that only perfectly matched sequences form stable duplexes. Under such conditions, the polynucleotides specifically hybridized through their tags may be ligated to the complementary sequences attached to the microparticles. Finally, the microparticles are washed to remove polynucleotides with unligated and/or mismatched tags.

Oligonucleotide tags can also be used for delivering labels to a plurality of kinds or subpopulations of polynucleotides, e.g. as encoded adaptors, as described in detail in co-owned U.S. Pat. No. 5,599,675, which is also incorporated by reference. Preferably, the length of single stranded tag complements for delivering labels is between 8 and 20, more preferably between 9 and 15.

III. Preparation of Reference Libraries

A reference DNA population may consist of any set of DNA sequences whose frequencies in different test populations is sought to be compared. Such a reference library could also be termed an "index library", since, in the context of the invention, it serves to provide a physically segregated array of clonal subpopulations of each DNA in the population.

Preferably, a reference DNA population for use in the analysis of gene expression in a plurality of cells or tissues is constructed by generating a cDNA library from each of the cells or tissues whose gene expression is being compared. This may be accomplished either by pooling the mRNA extracted from the various cells and/or tissues, or it may be accomplished by pooling the cDNAs of separately constructed cDNA libraries. The objective is to obtain a set of DNA sequences that will include all of the sequences that could possibly be expressed in any of the cells or tissues being analyzed.

For analysis of genetic variations between two genomic DNA samples of individuals or populations of individuals, genomic DNA is extracted from each of the individuals of a population of interest and pooled. The number of individuals in each of the populations is not critical; however, it is desirable to have the population sufficiently large so that many, if not all the polymorphic sequences of interest are captured. Preferably, the population consists of at least five individuals, and more preferably, it consists of at least ten individuals. Still more preferably, the population consists of a number of individuals in the range of from 10 to 100. When the genomic DNA is combined for processing, equal amounts are preferably contributed from each genome of the population.

Once the DNA sequences making up a reference DNA population are obtained, they are attached to discrete solid surfaces, e.g. separated microbeads or discrete regions of a planar array. In one embodiment, these reference DNA sequences are conjugated with oligonucleotide tags for solid phase cloning. Preferably, the DNA sequences are prepared so that they can be inserted into a vector carrying an appropriate tag repertoire, as described above, to form a library of tag-DNA sequence conjugates. A sample of conjugates is taken from this library, amplified, and loaded onto microparticles. It is important that the sample be large enough so that there is a high probability that all of the different types of DNA sequences are represented on the loaded microparticles. For example, if among a plurality of cells being compared a total of about 25,000 genes are expressed, then a sample of about five-fold this number, or about 125,000 tag-DNA sequence conjugates, should be taken to ensure that all possible DNA sequences will be represented among the loaded microparticles with about a 99% probability, e.g. Sambrook et al. (cited above).

For analysis of differential expression of genes, the reference library is a cDNA library. Preferably, clonal subpopulations of cDNAs are attached to microparticles using the processes described above and illustrated in FIGS. 3A and 3B. First, as illustrated in FIG. 3A, mRNA (300) is extracted from a cell or tissue source of interest using conventional techniques and is converted into cDNA (309) with ends appropriate for inserting into vector (316). Preferably, primer (302) having a 5' biotin (305) and poly(dT) region (306) is annealed to mRNA strands (300) so that the first strand of cDNA (309) is synthesized with a reverse transcriptase in the presence of the four deoxyribonucleoside triphosphates. Preferably, 5-methyldeoxycytidine triphosphate is used in place of deoxycytosine triphosphate in the first strand synthesis, so that cDNA (309) is hemimethylated, except for the region corresponding to primer (302). This allows primer (302) to contain a non-methylated restriction site for releasing the cDNA from a support. The use of biotin in primer (302) is not critical to the invention, and other molecular capture techniques, or moieties, can be used, e.g. triplex capture, or the like. Region (303) of primer (302) preferably contains a sequence of nucleotides that results in the formation of restriction site $r_2$ (304) upon synthesis of the second strand of cDNA (309). After isolation by binding the biotinylated cDNAs to streptavidin supports, e.g. Dynabeads M-280 (Dynal, Oslo, Norway), or the like, cDNA (309) is preferably cleaved with a restriction endonuclease which is insensitive to hemimethylation (of the C's) and which recognizes site $r_1$ (307). Preferably, $r_1$ is a four-base recognition site, e.g. corresponding to Dpn II, or like enzyme, which ensures that substantially all of the cDNAs are cleaved and that the same defined end is produced in all of the cDNAs. After washing, the cDNAs are then cleaved with a restriction endonuclease recognizing $r_2$, releasing fragment (308) which is purified using standard techniques, e.g. ethanol precipitation, polyacrylamide gel electrophoresis, or the like.

After resuspending in an appropriate buffer, fragment (308) is directionally ligated into vector (316), which carries tag (310) and a cloning site with ends (312) and (314). Preferably, vector (316) is prepared with a "stuffer" fragment in the cloning site to aid in the isolation of a fully cleaved vector for cloning.

For analysis of genomic variations among individuals or populations of individuals, genomic DNA is extracted from each of the individuals of a population of interest and pooled, and a reference population of restriction fragments is produced from the pooled genomic DNA. When the genomic DNA is combined for processing, equal amounts are preferably contributed from each genome of the population. The DNA is cleaved with first and second restriction endonucleases and ligated into a vector, e.g. as described above and shown in FIG. 3A.

Preferably, tag-DNA conjugates are carried in vector (330) (see FIG. 3B), which comprises the following sequence of elements: first primer binding site (332), restriction site $r_3$ (334), oligonucleotide tag (336), junction (338), DNA (340), restriction site $r_4$ (342), or (314) in FIG. 3A, and second primer binding site (344). After a sample is taken of the vectors containing tag-DNA conjugates, the following steps are implemented: The tag-DNA conjugates are preferably amplified from vector (330) by use of biotinylated primer (348) and labeled primer (346) in a conventional polymerase chain reaction (PCR) in the presence of 5-methyldeoxycytidine triphosphate, after which the resulting amplicon is isolated by streptavidin capture. Restriction site $r_3$ preferably corresponds to a rarecutting restriction endonuclease, such as Pac I, Not I, Fse I, Pme I, Swa I, or the like, which permits the captured amplicon to be released from a support with minimal probability of cleavage occurring at a site internal to the DNA of the amplicon. Junction (338), which is illustrated as the sequence:

5' . . . GGGCCC . . .

3' . . . CCCGGG . . .

causes the DNA polymerase "stripping" reaction to be halted at the G triplet, when an appropriate DNA polymerase is used with dGTP. Briefly, in the "stripping" reaction, the 3'→5' exonuclease activity of a DNA polymerase, preferably T4 DNA polymerase, is used to render the tag of the tag-DNA conjugate single stranded, as taught by Brenner, U.S. Pat. No. 5,604,097, and Kuijper et al., Gene 112: 147–155 (1992). In a preferred embodiment, where sorting is accomplished by formation of duplexes between tags and tag complements, tags of tag-DNA conjugates are rendered single stranded by first selecting words that contain only three of the four natural nucleotides, and then by preferentially digesting the three nucleotide types from the tag-DNA conjugate in the 3'→5' direction with the 3'→5' exonuclease activity of a DNA polymerase. In the preferred embodiment, oligonucleotide tags are designed to contain only A's, G's, and T's; thus, tag complements (including that in the double stranded tag-DNA conjugate) consist of only A's, C's, and T's. When the released tag-DNA conjugates are treated with T4 DNA polymerase in the presence of dGTP, the complementary strands of the tags are "stripped" away to the first G. At that point, the incorporation of dG by the DNA polymerase balances the exonuclease activity of the DNA polymerase, effectively halting the "stripping" reaction. From the above description, it is clear that one of ordinary skill could make many alternative design choices for carrying out the same objective, i.e. rendering the tags single stranded. Such choices could include selection of different enzymes, different compositions of words making up the tags, and the like.

When the "stripping" reaction is quenched, the result is duplex (356) with single stranded tag (357). After isolation, steps (358) are implemented: the tag-DNA conjugates are hybridized to tag complements attached to microparticles, a fill-in reaction is carried out to fill any gap between the complementary strand of the tag-DNA conjugate and the 5' end of tag complement (362) attached to microparticle (360), and the complementary strand of the tag-DNA conjugate is covalently bonded to the 5' end (363) of tag complement (362) by treating with a ligase. This embodiment requires, of course, that the 5' end of the tag complement be phosphorylated, e.g. by a kinase, such as, T4 polynucleotide kinase, or the like. The fill-in reaction is preferably carried out because the "stripping" reaction does not always halt at the first G. Preferably, the fill-in reaction uses a DNA polymerase lacking 5'→3' exonuclease activity and strand displacement activity, such as T4 DNA polymerase. Also preferably, all four dNTPs are used in the fill-in reaction, in case the "stripping" extended beyond the G triplet. Preferably, after the tag-DNA sequence conjugates are sampled, they are amplified by PCR using a fluorescently labeled primer (346) to provide sufficient material to load onto the tag complements of the microparticles and to provide a means for distinguishing loaded from unloaded microparticles, as disclosed in Brenner et al., U.S. Pat. No. 5,604,097.

The tag-DNA conjugates are preferably hybridized to the full repertoire of tag complements. That is, among the population of microparticles, there are microparticles having every tag sequence of the entire repertoire. Thus, the tag-DNA conjugates will generally hybridize to tag complements on only about one percent of the microparticles. Loaded microparticles are separated from unloaded microparticles for further processing, as noted above, preferably by use of a fluorescence-activated cell sorter (FACS). In the embodiment illustrated in FIG. 3B, a fluorescent label, e.g. FAM, is attached by way of primer (346).

Figure 3C:
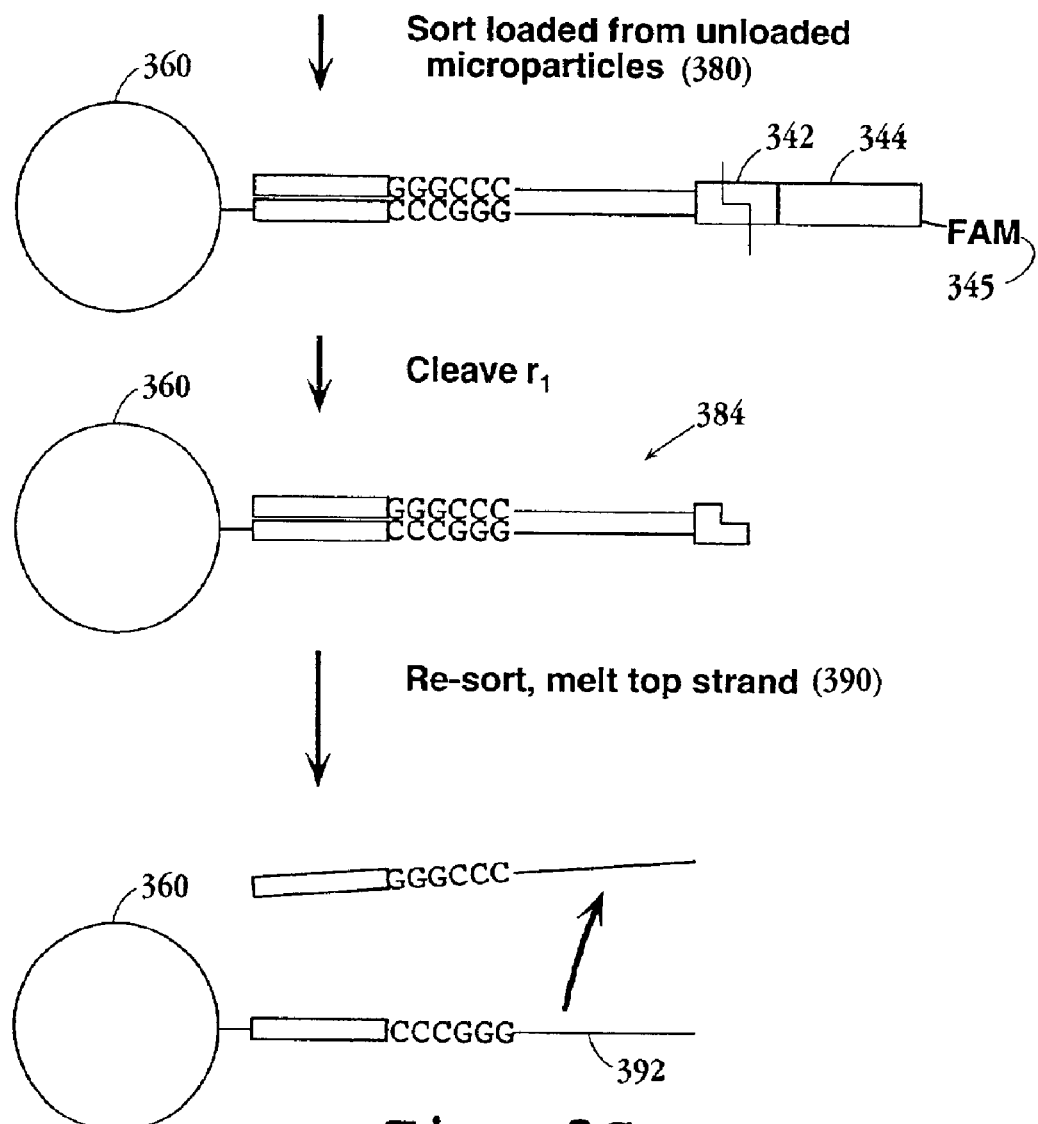
FIG. 3C illustrates a preferred scheme for isolating DNA-loaded microparticles and preparing the reference library for competitive hybridization.

As shown in FIG. 3C, after FACS, or like sorting (380), loaded microparticles (360) are isolated, treated to remove label (345), and treated to melt off the non-covalently attached strand. Preferably, the tag-DNA conjugates are treated with a restriction endonuclease recognizing site $r_1$ (342) which cleaves the tag-DNA conjugates adjacent to primer binding site (344), thereby removing label (345) carried by the "bottom" strand, i.e. the strand have its 5' end distal to the microparticle. The top strand is then melted off (e.g. by treatment with NaOH) to leave a covalently attached single strand of the DNA (392) ready to accept single stranded DNAs or mRNAs in a competitive hybridization assay, as described further below.

In another embodiment, DNA sequences of the reference library are amplified and prepared separately, and attached onto the discrete solid surfaces separately before being combined into a reference library. In still another embodiment, the DNA sequences are cloned and end labeled with a biotin moiety separately, and such prepared DNAs are attached to streptavidin coated microbeads separately before combination.

IV. Competitive Hybridization and Light-Generating Labels

Probes to be used in competitive hybridization are derived from gene expression products, e.g. mRNA or cDNA, from the cells and/or tissues being analyzed, or from genomic DNA fragments, as described further below. These probes can be labeled, if desired, by conventional methods, such as reverse transcription of mRNA in the presence of a labeled nucleoside triphosphate, e.g. Schena et al. or DeRisi et al., (cited above), or by incorporation of a capture moiety, such as an amine-labeled dNTP, biotinylated nucleoside triphosphates or an oligonucleotide tag, followed by complexing with a moiety capable of generating a fluorescent signal, such as an amine-reactive fluorescent dye, a streptavidin-fluorescent dye conjugate or a labeled tag complement.

Preferably, for SID sequence-containing DNA probes prepared for FACS sorting as described below, labels are incorporated by employing a labeled primer in PCR amplification of probe-adaptor conjugates which are used for preparation of the SID-containing probes. Alternatively, labeled decoder molecules are attached to the SID sequences following competitive hybridization, as discussed further below.

A large number of light-generating labels are available, including fluorescent, calorimetric, chemiluminescent, and electroluminescent labels. Generally, such labels produce an optical signal which may comprise an absorption frequency, an emission frequency, an intensity, a signal lifetime, or a combination of such characteristics. Preferably, fluorescent labels are employed. Preferably, the optical signal detected from a fluorescent label is an intensity at one or more characteristic emission frequencies. Selection of fluorescent dyes and means for attaching or incorporating them into DNA strands is well known, e.g. DeRisi et al. (cited above), Matthews et al., *Anal. Biochem.* 169: 1–25 (1988); Haugland, *Handbook of Fluorescent Probes and Research Chemicals* (Molecular Probes, Inc., Eugene, 1992); Keller and Manak, *DNA Probes*, 2nd Edition (Stockton Press, New York, 1993); and Eckstein, editor, *Oligonucleotides and Analogues: A Practical Approach* (IRL Press, Oxford, 1991); Wetmnur, *Critical Reviews in Biochemistry and Molecular Biology* 26: 227–259 (1991); Ju et al., *Proc. Natl. Acad. Sci.* 92: 4347–4351 (1995); and Ju et al., *Nature Medicine* 2: 246–249 (1996); and the like.

Preferably, light-generating labels are selected so that their respective optical signals can be related to the quantity of labeled DNA strands present and so that the optical signals generated by different light-generating labels can be compared. Measurement of the emission intensities of fluorescent labels is the preferred means of meeting this design objective. For a given selection of fluorescent dyes, relating their emission intensities to the respective quantities of labeled DNA strands requires consideration of several factors, including fluorescent emission maxima of the different dyes, quantum yields, emission bandwidths, absorption maxima, absorption bandwidths, nature of excitation light source(s), and the like. Guidance for making fluorescent intensity measurements and for relating them to quantities of analytes is available in the literature relating to chemical and molecular analysis, e.g. Guilbault, editor, *Practical Fluorescence*, Second Edition (Marcel Dekker, New York, 1990); Pesce et al., editors, *Fluorescence Spectroscopy* (Marcel Dekker, New York, 1971); White et al., *Fluorescence Analysis: A Practical Approach* (Marcel Dekker, New York, 1970); and the like.

As used herein, the term "relative optical signal" means a ratio of signals from different light-generating labels that can be related to a ratio of differently labeled DNA strands of identical, or substantially identical, sequence that form duplexes with a complementary reference DNA strand. Preferably, a relative optical signal is a ratio of fluorescence intensities of two or more different fluorescent dyes.

Competitive hybridization between the probe DNA strands derived from the plurality of cells, tissues or individuals is carried out by applying equal quantities of the total probe DNA from each of two such sources to the microparticles loaded with the reference DNA population. Hybridization is competitive in that probe DNA strands with identical, or substantially identical, sequences compete to hybridize to the same complementary reference DNA strands. The competitive hybridization conditions are selected so that the ratio of the two corresponding probe DNA strands forming duplexes with complementary reference DNA strands reflects, and preferably is directly proportional to, the ratio of the amount of that DNA strand in its population to the amount of the competing DNA strands of identical sequence in their respective population. Thus, if first and second probe DNA strands from different sources, but with identical sequence, are competing for hybridization with a complementary reference DNA strand, and the first probe DNA strand is at a concentration of 1 ng/$\mu$l while the second probe DNA strand is at a concentration of 2 ng/$\mu$l, then at equilibrium it is expected that one third of the duplexes formed with the reference DNA would include first probe DNA strands and two thirds of the duplexes would include second probe DNA strands. Guidance for selecting hybridization conditions is provided in many references, including Keller and Manak, (cited above); Wetmur, (cited above); Hames et al., editors, *Nucleic Acid Hybridization: A Practical Approach* (IRL Press, Oxford, 1985); and the like.

The particular amounts of probe DNA added to the competitive hybridization reaction vary widely depending on the embodiment of the invention. Factors influencing the selection of such amounts include, for example, the structure of probes (single or double stranded), the volume of the hybridization reaction, the quantity of microparticles used, the type of microparticles used, the loading of reference DNA strands on the microparticles, the complexity of the populations of probe DNA, and the like. For example, the amount of probe DNA which would theoretically be required to hybridize to every strand of DNA on a library of microbeads can be estimated from the loading (i.e. the number of reference DNA molecules per bead), the number of beads used, and the average molecular weight of the probe DNA. In practice, this amount is typically multiplied by a factor of about 10–100.

V. Flow Sorting of Microparticles with Unequally Represented Probe Sequences

A. SRQ Methods

Microparticles containing fluorescently labeled DNA strands are conveniently classified and sorted by a commercially available FACS instrument, e.g. Van Dilla et al., *Flow Cytometry: Instrumentation and Data Analysis* (Academic Press, New York, 1985). For fluorescently labeled DNA strands competitively hybridized to a reference strand, preferably the FACS instrument has multiple fluorescent channel capabilities. Preferably, upon excitation with one or more high intensity light sources, such as a laser, a mercury arc lamp, or the like, each microparticle generates fluorescent signals, usually fluorescence intensities, which are related to the quantity of labeled DNA strands from each sample carried by the microparticle.

Figure 1B:
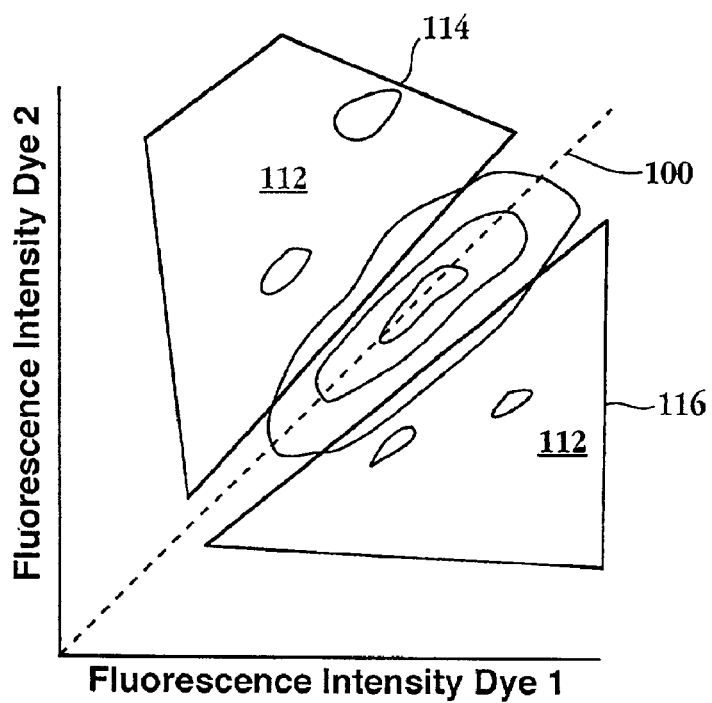

As shown in FIG. 1A, when fluorescent intensities of each microparticle are plotted on a two-dimensional graph, microparticles indicating equal expression levels are on or near the diagonal (100) of the graph. Up-regulated and down-regulated genes appear in the off-diagonal regions (112). Such microparticles are readily sorted by commercial FACS instruments by graphically defining sorting parameters to enclose one or both off-diagonal regions (112) as shown in FIG. 1B.

The present invention provides, in one aspect, a FACS method for high resolution sorting of microbead-supported DNA clones, based on what is termed herein probe subtraction (or SID) remainder quantification, or SRQ (FIG. 2a). In accordance with this method, the DNA probes (labeled or unlabeled) prepared from the two different sample sources being compared are tagged with two different sample identifier (SID) sequences, termed first SID and second SID sequences, respectively. The SID sequences are appended at the terminus which, upon hybridization of the probe to the reference DNA, will be remote from the bead surface. After hybridization of the probes onto the reference DNA strands on the solid support, the respective SID sequences from the two different probes are able to hybridize to each other in a 1:1 ratio. The first and second SID sequences may be complementary, such that they hybridize to each other directly, or they may hybridize indirectly through an intermediate molecule, e.g. an oligonucleotide whose terminal sequences are complementary to each of the SID sequences. A molecule having two such terminal sequences connected by a non-oligonucleotide linker, e.g. an alkyl or PEG chain, or a PNA segment, could also be used.

Upon such hybridization, the amount of SID sequence (first or second) present in a lesser quantity is "subtracted" from the amount of the other SID sequence on the same bead. The remainder of this subtraction, that is, the quantity of first or second SID sequences remaining unhybridized (also referred to as "remainder" sequences), represents the absolute molar difference between the two probes of different sources hybridized to the given solid support.

For detection purposes, labeled decoder (or reporter) molecules are applied to the unhybridized SID ("remainder") sequences. A pair of decoders is used, each of which is selectively attachable to a particular "remainder" sequence, and each having a different light-generating label, preferably a fluorescent dye (see FIG. 2A). Decoder molecules are typically oligonucleotides having a terminal sequence complementary to the first SID or second SID sequence, respectively, and bearing at least one or a plurality of fluorescent dye molecules. (See FIG. 2B.) The decoder may be ligated to the SID remainders after annealing, as described in Example 5.

Figure 4A:
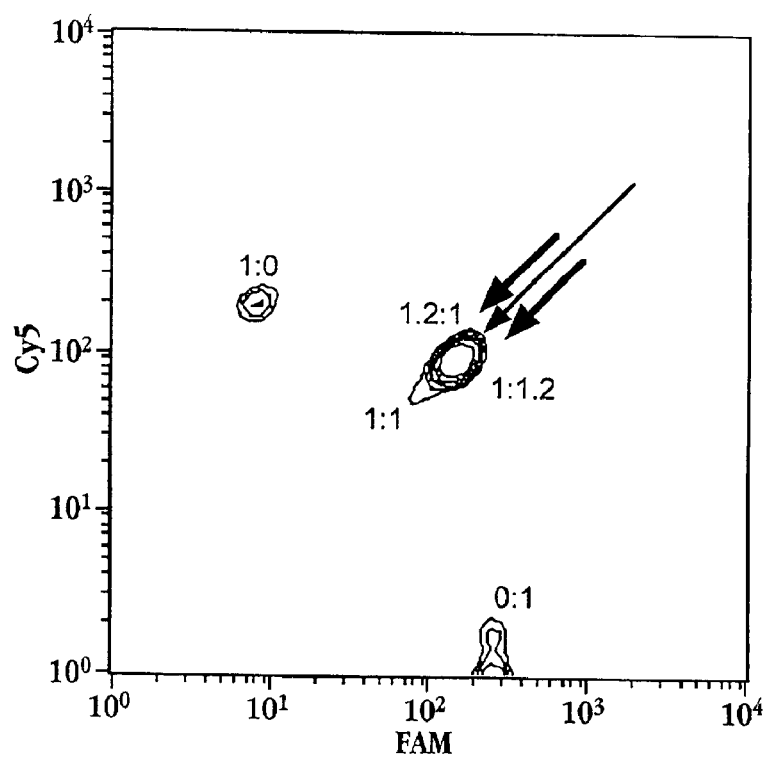
FIGS. 4A–C show FACS sorting data for beads having a 1.2:1 ratio of probes from different sample populations, using: labeled probes only, with no SID sequence tags (control) (a), unlabeled SRQ probes with labeled decoders (b), and unlabeled SRQ probes with multiply labeled decoders (c)
Figure 4B:
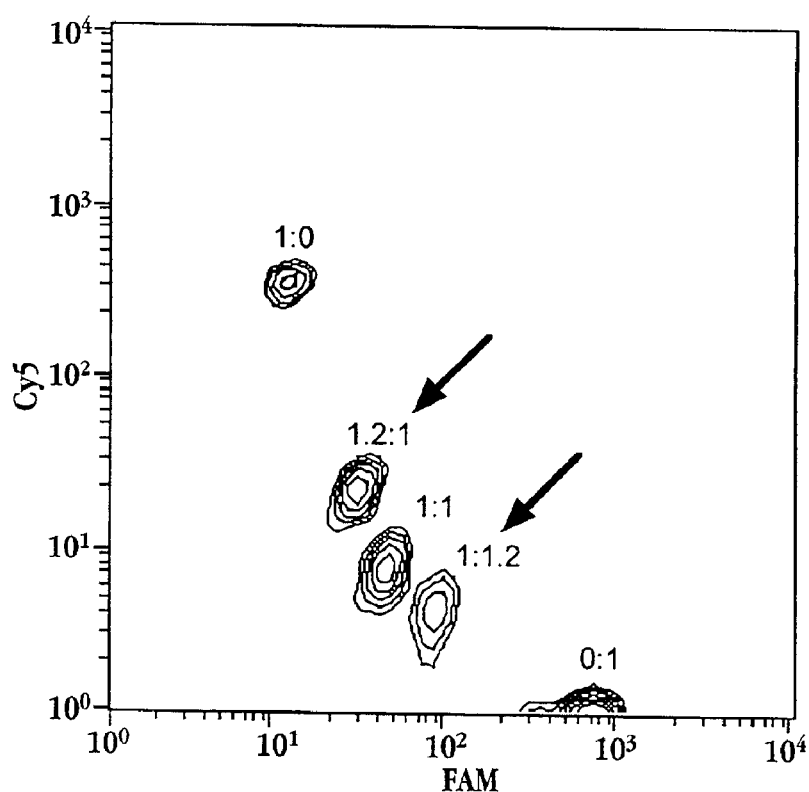
Figure 4C:
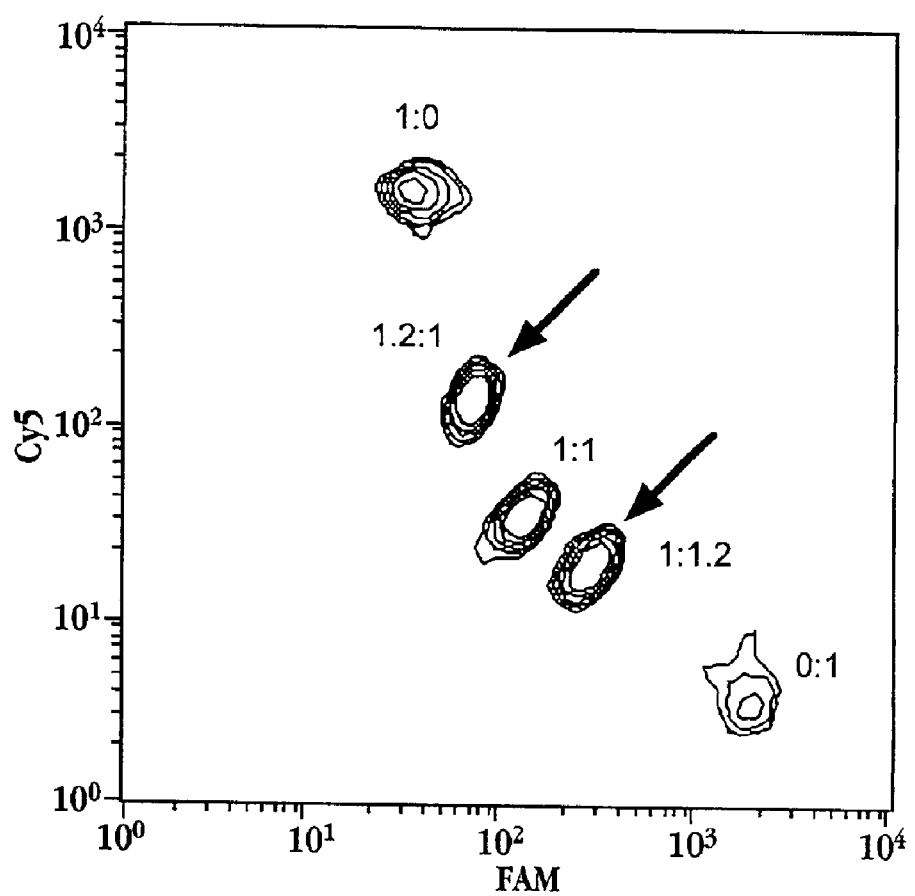

FIG. 4 shows enhancement of the fluorescent signal ratio from an assay (described further below) of beads having a 1.2:1 ratio of probes from two different samples, employing unlabeled probes and labeled decoder molecules, either singly labeled (FIG. 4B) or multiply labeled (4C), in comparison to non-SRQ FACS sorting, using labeled probes only (control, FIG. 4A). As can be seen from the Figures, and the schematic in FIG. 2B, the ratio can be enhanced several times by the use of multiply labeled decoders. A multiply labeled decoder may comprise a longer oligonucleotide having a terminal sequence complementary to the first SID or second SED sequence, respectively, and a further sequence containing multiple copies of a short repeating sequence. Multiple short oligonucleotides which are complementary to the repeating sequence and which bear a label can be hybridized to the longer oligonucleotide to form a multiply labeled decoder molecule.

Figure 5A:
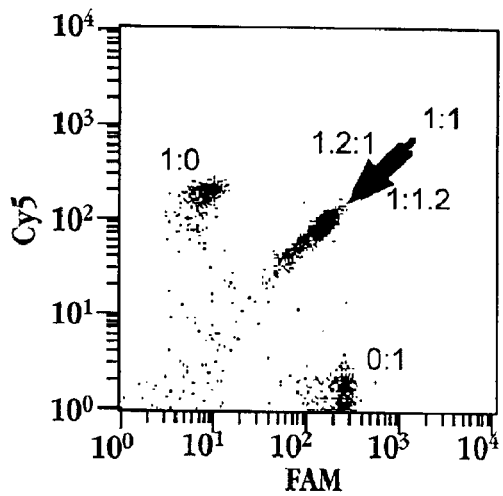
FIGS. 5A–C show FACS sorting data as described for FIGS. 4A–C, but where the SRQ probes are labeled.
Figure 5B:
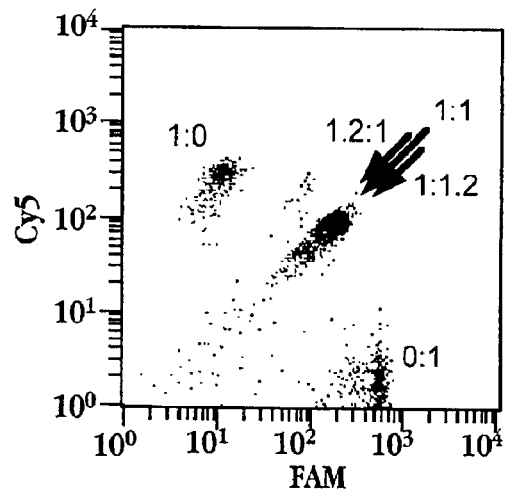
Figure 5C:
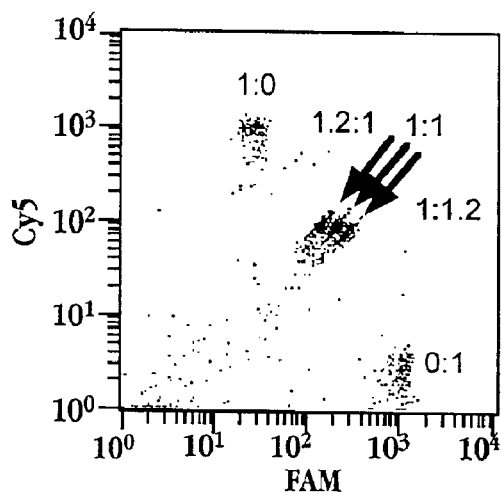
Figure 6A:
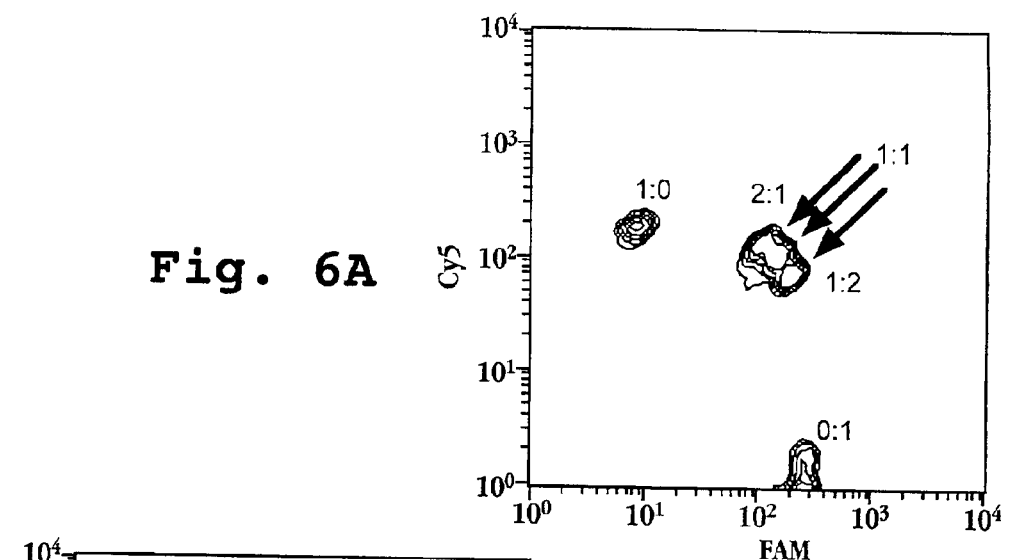
FIGS. 6A–C show FACS sorting data for beads having a 2:1 ratio of probes from different sample populations, using: labeled probes only, with no SID sequence tags (control) (a), labeled SRQ probes with labeled decoders (b), and labeled SRQ probes with multiply labeled decoders (c)
Figure 6B:
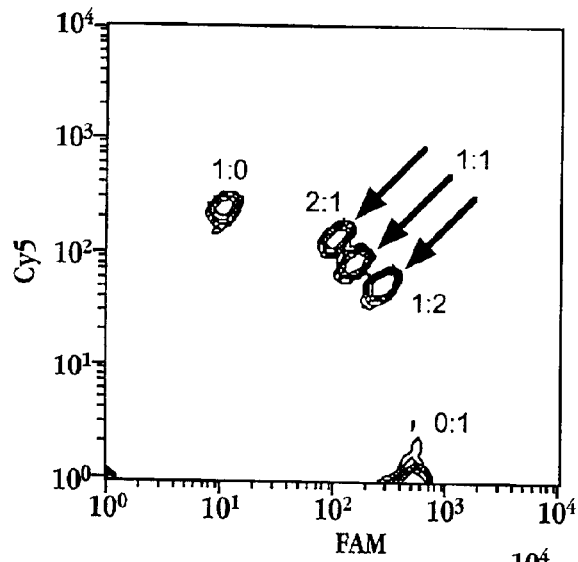
Figure 6C:
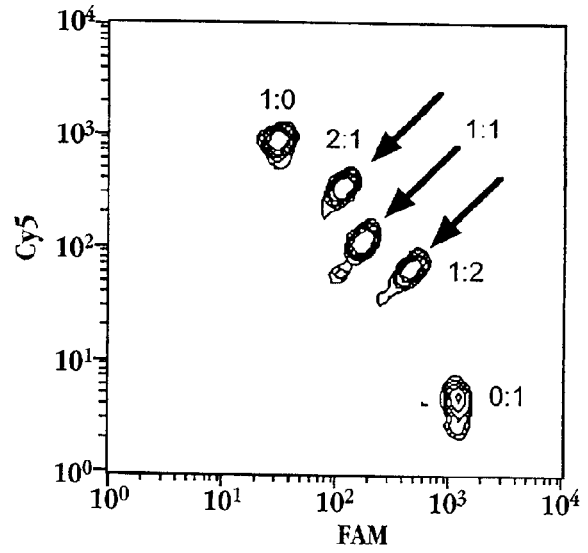

The probes may themselves be labeled, preferably with the same dye used to label the decoder moiety which eventually is attached to the probe SID sequence. FIGS. 5A–C show enhancement of the fluorescent signal ratio from an assay of beads having a 1.2:1 ratio of probes from different sample populations, employing labeled probes and labeled decoder molecules, which are either singly labeled (FIG. 5B) or multiply labeled (5C), in comparison to non-SRQ FACS sorting, using labeled probes only (control, FIG. 5A). FIGS. 6A–C show similar data for an assay of beads having a 2:1 ratio of probes from different sample populations.

When unlabeled probes are used, only the probe present in excess produces a signal, in theory (since only this probe will have a decoder molecule attached); therefore a greater signal ratio enhancement is expected than when the probes are also labeled. It can also be appreciated that, when the probes are unlabeled, the fluorescent signal represents the absolute difference between the two probes, rather than a ratio. Information about the ratio of probes can be desirable, since, for example, the absolute difference in a 100:95 ratio of probes will be the same as that in a (much higher) ratio of 10:5.

Accordingly, in one embodiment of the method, a known fraction of the probes are labeled. This combination of partially labeled probes with labeled decoder molecules, which may be multiply labeled, gives a highly enhanced signal (see the schematic in FIG. 2B and the data in FIGS. 7–8, discussed further below) and also provides information about the ratio of probes on a microparticle.

B. Preparation of Probes

The desired reference library is prepared from an appropriate reference DNA source (e.g. pooled genomic DNA or cDNA) by preparing a restriction digest, cloning, and loading each cloned fragment onto a spatially discrete solid support, e.g. a microparticle, preferably employing the loading methods described above. Probes are prepared from the sources of DNA being analyzed (i.e. compared to the reference DNA) by preparing a similar restriction digest and appending SID tags to the fragments, as described below. Various restriction enzymes, in addition to those shown, could be used in preparing the libraries and probes, in accordance with ordinary skill in the art.

Preparation of SID sequence-tagged probes for a model system is described in Example 5. Briefly, in the system described, the reference library is a "monobead" library, containing a single sequence from the human Y chromosome, designated TTY2.1 (Makrinou et al., *Genome Res.* 2001 Jun; 11(6):935–945). Of course, any reference DNA sequence of appropriate length could be used. To prepare the probes, the probe DNA, in this case a TTY2.1 plasmid clone, is modified with an insert of one of two adaptors (here designated MQ and FQ; SEQ ID NOs:4–9), each containing a first SID or second SID sequence, respectively (in boldface below), and an EarI restriction site sequence (underlined below). The EarI site is positioned relative to the SID tag such that cleavage of the adaptor will leave only the SID tag attached to the probe sequence. Note that probes could be designed by one skilled in the art containing other restriction sites for processing by their corresponding restriction enzymes.

```
MQ-adaptor
5'pATCGAGAGAAGAGCGTGCACAGGAA                  (SEQ ID NO:4)
     CTCTCTTCTCGCACGTGTCCTT-5'                (SEQ ID NO:5)

5'Biotin-TTCCTGTGCACGCTCTTCT - PCR primer     (SEQ ID NO:6)

FQ-adaptor
5'pATCCTCAGAAGAGCGTGCACTCCGA                  (SEQ ID NO:7)
     GAGTCTTCTCGCACGTGAGGCT-5'                (SEQ ID NO:8)

5'Biotin-TCGGAGTGCACGCTCTTCT - PCR primer     (SEQ ID NO:9)
```

The constructs were then amplified by PCR and purified. The PCR products were digested with EarI, leaving only the SID sequences attached to the probes, and end repaired with dNTPs using Klenow DNA polymerase, to generate the full length, SID-tagged double stranded DNA probes. After biotin affinity purification, these were converted to single stranded probes using λ exonuclease.

Labeled probes can be prepared, if desired, by using dye-labeled PCR primers (a different dye for each of the two adaptors), or by incorporating a dye-labeled nucleotide. However, the former method is preferable since it allows greater control of label incorporation and enhances the relative effect of the decoder signals, and labeled nucleotides are known to inhibit polymerase activity.

Figure 9A:
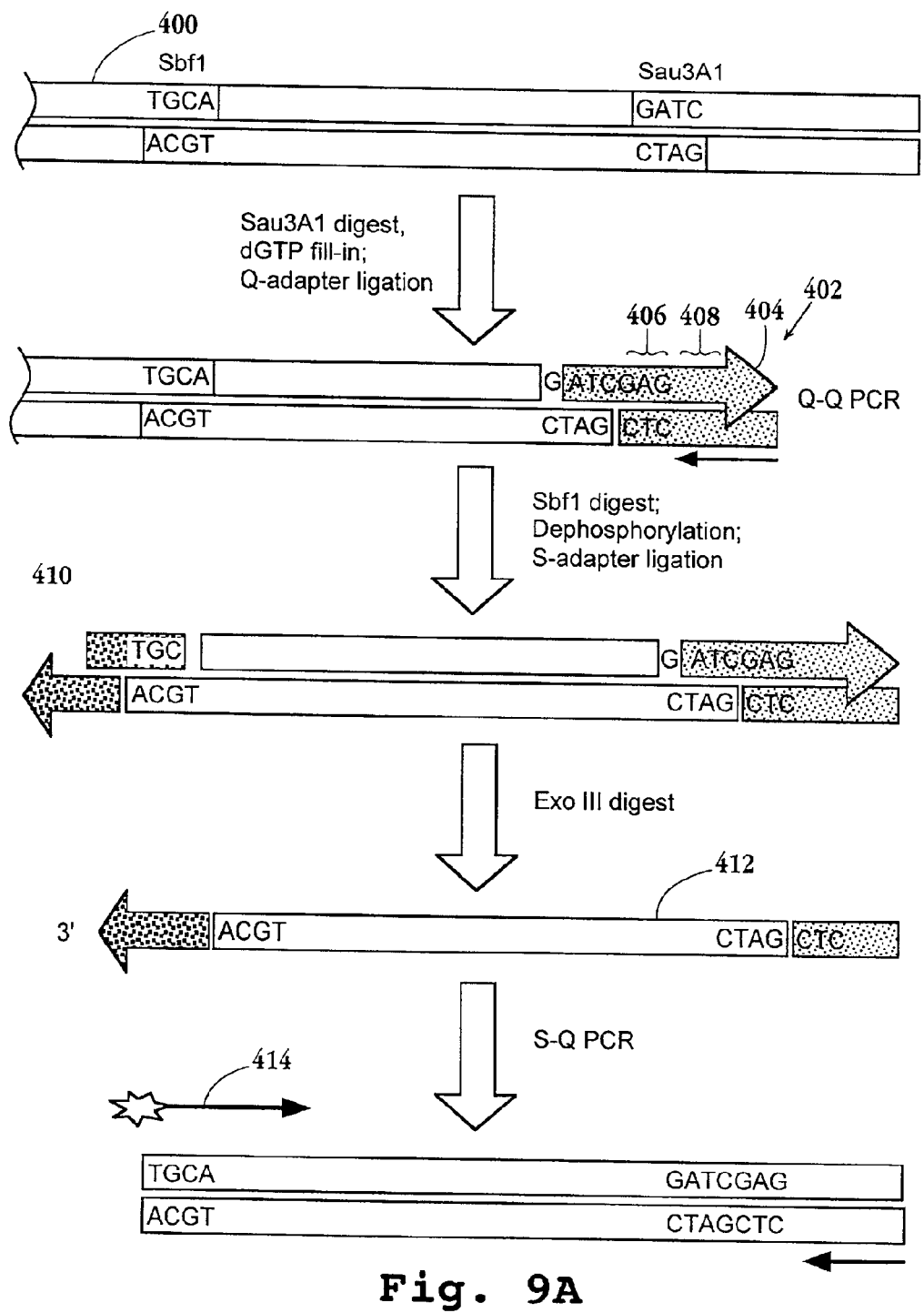
FIGS. 9A–B show a procedure for the preparation of SID sequence-tagged probe libraries from genomic DNA, as described in Example 6.
Figure 9B:
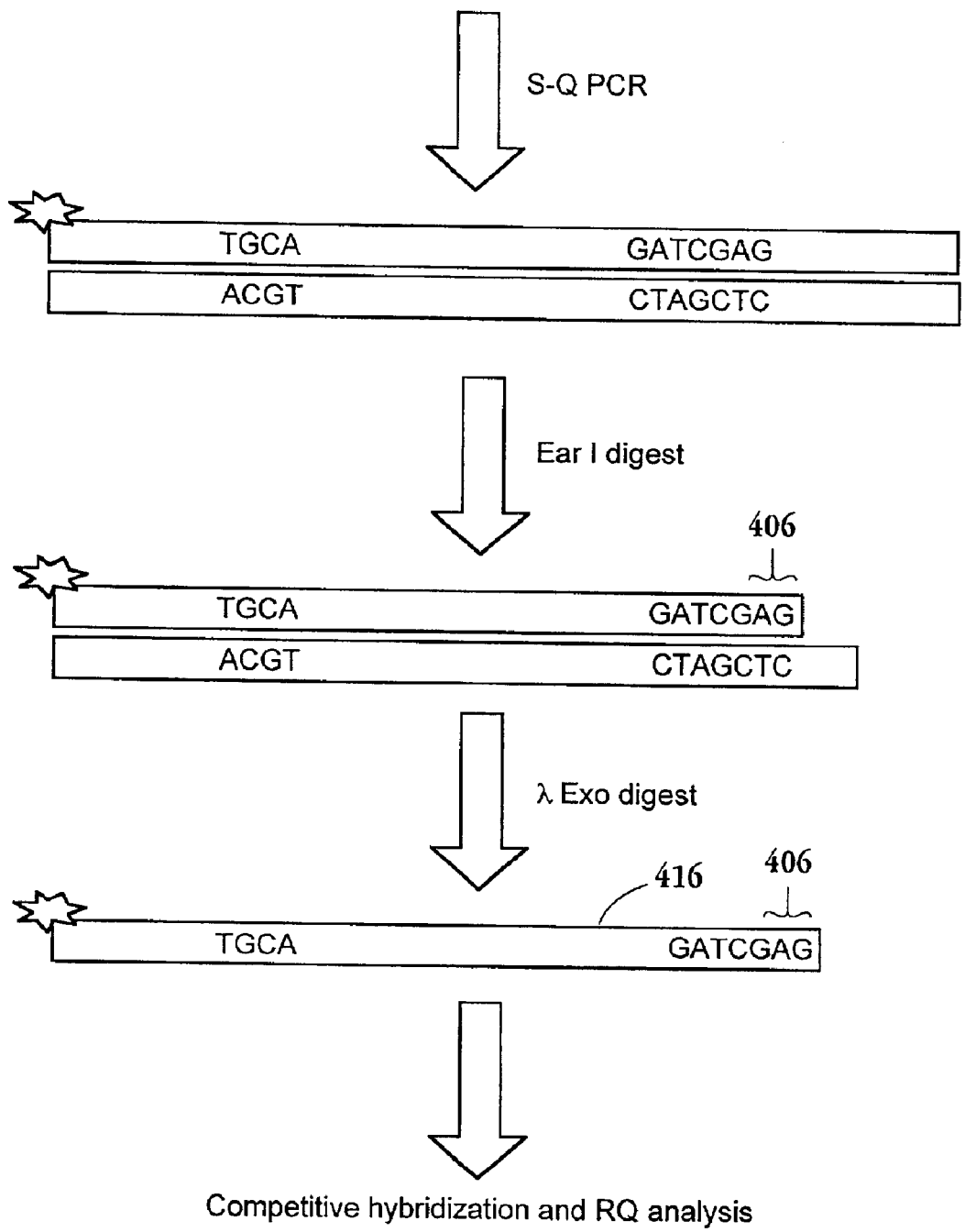

Preparation of probe libraries, e.g. from a genomic DNA or cDNA library, can be carried out as illustrated in FIGS. 9A–B. See also Example 6, below. As in preparation of the reference libraries, the DNA (400) is cleaved with a first restriction endonuclease, e.g. Dpn II or Sau3A, as illustrated in FIG. 9A, to produce a population of restriction fragments. FIG. 9A shows one terminus of a restriction fragment of genomic DNA. The restriction endonuclease may be any restriction enzyme whose cleavage results in fragments with predictable protruding strands, preferably at least four nucleotides in length. In further preference, the restriction endonuclease produces fragments having ends with 5' protruding strands, which allows the 3' recessed strands to be extended with a DNA polymerase in the presence of the appropriate nucleoside triphosphates.

Q adaptors (402) are then ligated to the cleaved ends, in a conventional ligation reaction, to give fragment-adaptor complexes. In a preferred embodiment, the 3' recessed strands of such fragments are first extended by one nucleotide ("dGTP fill-in" in the Figure) to reduce the length of the protruding strands to three nucleotides, thereby destroying the self-complementarity of the protruding strand. This step helps to reduce self-ligation, both of the fragments and the Q adaptors.

Q adaptors, and S adaptors, described below, are double stranded oligonucleotide adaptors which contain complementary protruding strands to those of the restriction fragments. Q adaptors may vary widely in length and composition, but are preferably long enough to include a primer binding site (404) for amplifying the fragment-adaptor complexes by polymerase chain reaction (PCR). Preferably, the double stranded region of Q adaptors is within the range of 14 to 30 basepairs, and more preferably, within the range of 16 to 24 basepairs. Q adaptors for use in the present invention also contain a first or second SID sequence (406) and an EarI restriction site (408), adjacent to the SID sequence, for later removal of the portion of the adaptor beyond the SID sequence.

The genomic fragments, having a Q adaptor on each end, are then amplified by "Q—Q" PCR and purified. The amplified fragment-adaptor complexes are then digested with a second restriction endonuclease, e.g. Sbf1 as shown in FIGS. 9A–B, and dephosphorylated at the cleaved 5' end. A second adaptor, termed an S adaptor (410), is then ligated to the cleaved ends. The use of different adaptors allows greater control in PCR amplification, such that either the top or bottom strand can be labeled. The top strand is then removed by digestion with Exonuclease III or similar acting exonuclease, to suppress the amplification of DNA fragments without any Sbf1 site in the later PCR step. The bottom strand (412) is then amplified by "Q–S" PCR, using a labeled S primer (414), as shown in the Figure, if labeling of the probes is desired. In the PCR amplification, 5-Me-CTP is preferably used to protect internal EarI sites from later digestion.

Figure 10:
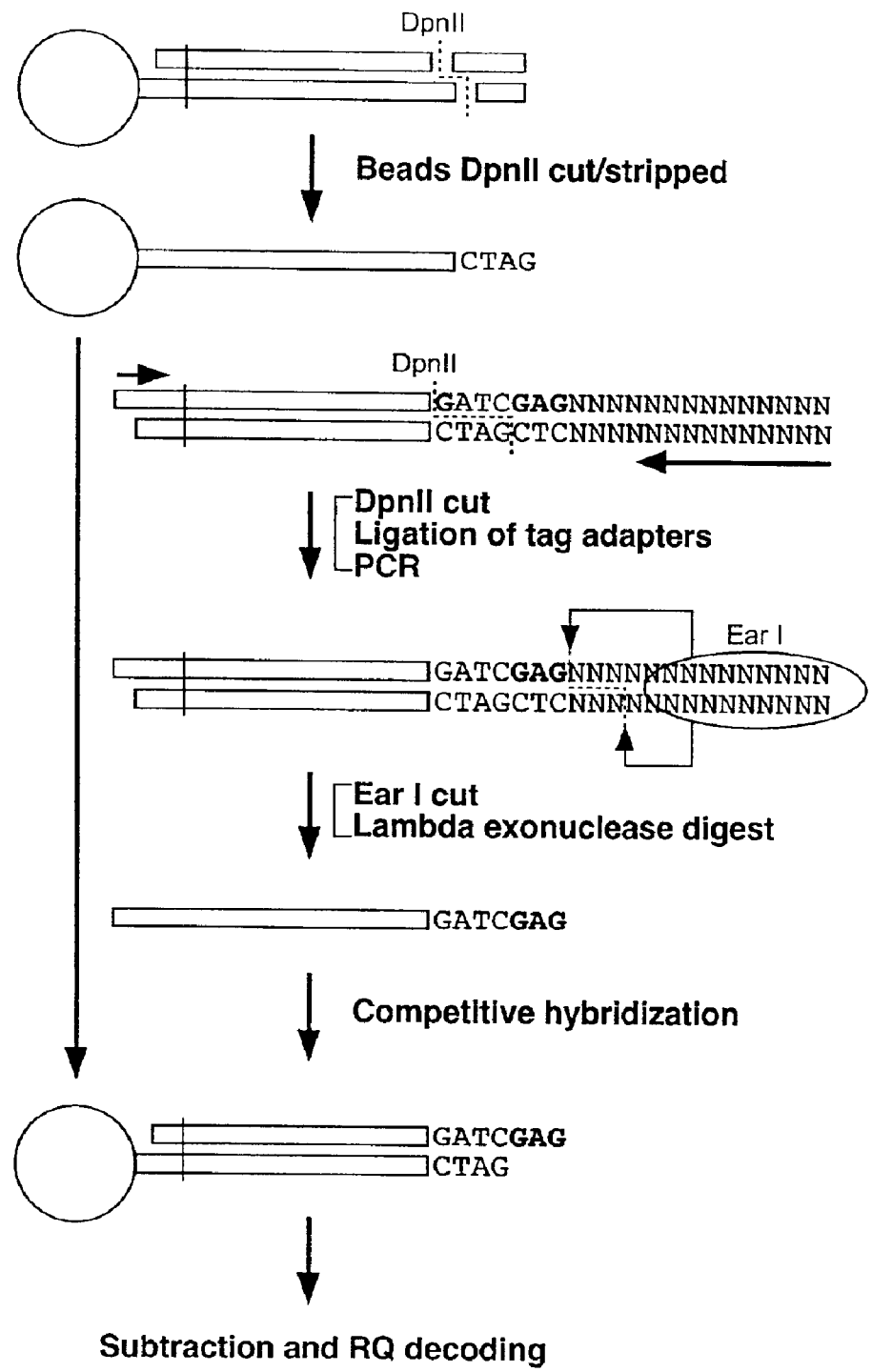
FIG. 10 shows a schematic illustration of the preparation of a reference library and SID sequence-tagged probe libraries for SRQ competitive hybridization.

The double stranded probes (FIG. 9B) are then digested with Ear I, which cleaves the Q adaptor and leaves the SID tag (406) on the top strand of the probe. The bottom strand is digested with λ exonuclease, starting at the 5' phosphate, leaving the single-stranded probe (416) for competitive hybridization. It will be appreciated that these strands are complementary (with the exception of the 3' SID tag of the probe) to the bottom strands attached to the beads in the reference library preparation illustrated in FIG. 3C. See also the schematic illustration of the process in FIG. 10, where the top of the figure illustrates steps in the formation of the reference library on microbeads, the central portion illustrates steps in preparation of the corresponding probes, and hybridization of a probe, with SID sequence, to the microbead is shown at the bottom of the figure.

When unlabeled probes are prepared (so that primers need not be labeled), a preferred method of preparation employs co-amplification of the two probes; that is, performing PCR on a mixture of the two probe-adaptor constructs described above from the two samples. This method avoids any PCR bias in preparation of the probes.

C. Assay Parameters and Conditions

The probe ends bearing the first SID and second SID sequences must be close enough for annealing and ligation once competitive hybridization of the probes is complete. This proximity is determined by the length of the probes and the DNA loading on the microbeads. For example, the loaded DNA molecules in the system described in Example 5 are 236 bp long (including a 28 mer spacer and 32 mer 8-word tag sequence used for sorting and loading, as described above), which is equivalent to a length of about 80 nm. The distance between DNA attachment points on the microbeads should be less than approximately 160 nm (2×80 nm) to ensure that the first SID and second SID sequences, which will be located adjacent the ends of the DNA molecules, are able to hybridize. This translates approximately to a minimum effective hybridization of $4 \times 10^3$ probe molecules/microbead. Efficiency of probe hybridization and end annealing must also be considered. For most applications, reference DNA loading of $10^4$ DNA/bead or higher is preferred. For example, in the procedures described in Example 5, competitive hybridization is carried out by incubating, for 16 h at 65° C., 20,000 reference library beads with 100 ng ssDNA probe in 100 μl of buffer.

Following competitive hybridization, the SRQ process is carried out, under conditions which facilitate intra-bead annealing between the two types of SID sequences and between the remainder sequences and corresponding decoder molecules. Lower concentrations of beads and higher concentrations of decoder molecules are generally favored. The suspension is then treated with ATP and ligase for (i) ligation of the hybridized SID sequences and (ii) attachment and ligation of the decoder molecules. Reaction (i) is expected to occur rapidly, since the hybridizing sequences are on the same bead, while (ii), in which the decoder molecules are in solution, occurs more slowly. Preferably, ATP and ligase are added, then, after a short reaction time (approx. 3 minutes or less), the decoder mixture is added. However, the reagents may also be added simultaneously. These steps are typically carried out at room temperature or below. In the system described in Example 5, since short SID sequences are used (3 nt), ligation is carried out at 16° C. to stabilize the SID sequence duplexes.

Longer SID sequences can be used, and may be advantageous in that the duplexes are more stable; therefore, ligation of the duplexes, and of decoder molecules to the remainders, is less likely to be required. Generally, ligation is not required if the SID sequences are 15 nucleotides or more in length.

If desired, magnet activated cell sorting (MACS) may be used to presort remainder-containing probes (that is, those having unhybridized SID sequences), which frequently represent a small fraction of the whole, from the background; that is, the 1:1 probe ratio beads. This may be done by using a magnetically labeled SID sequence decoder to label remainder-containing beads, and setting separation force parameters to facilitate isolation of such beads. After this MACS-presorting, the MACS decoders are removed, and the beads are labeled with fluorescent decoders and subjected to FACS sorting as described above. Alternatively, or in addition, a second FACS sorting of a selected population of beads can reduce any instrument sampling error.

D. Results: Comparison with Conventional Probe Ratio FACS

FIGS. 4–8, discussed above, show the effectiveness of the method in enhancing the optical signal ratio relative to the ratio of the probes from the two samples, and thereby increasing the precision with which solid supports having differing ratios of probes can be sorted from those having DNA clones equally represented between the two samples being compared. The model system (see Example 5) used a monobead reference library, i.e. a microbead library of a single monoclonal DNA sequence of 176 bp from the human Y-chromosome. In all cases, the observed ratio of fluorescent signals on bead populations with unequal molar amounts of the two probes were enhanced relative to the original ratios of probes hybridized onto the beads. The observed ratio of the two fluorescent signals on a bead population with equimolar amounts of two probes remained unchanged, as expected.

Figure 7A:
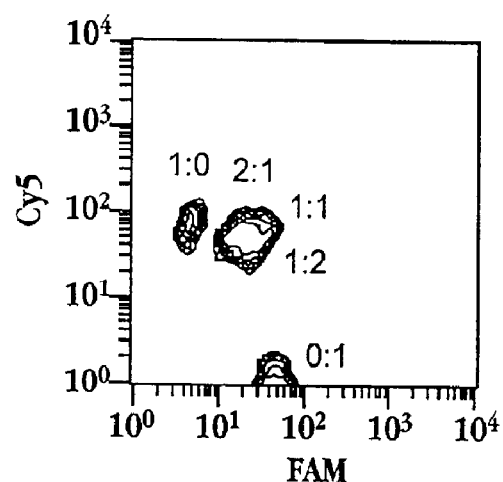
FIGS. 7A–D show FACS sorting data for beads having a 2:1 ratio of probes from different sample populations, using: labeled probes only, with no SID sequence tags (control) (a), labeled SRQ probes with labeled decoders (b), partially labeled SRQ probes with labeled decoders (c), and unlabeled SRQ probes with labeled decoders (d)
Figure 7B:
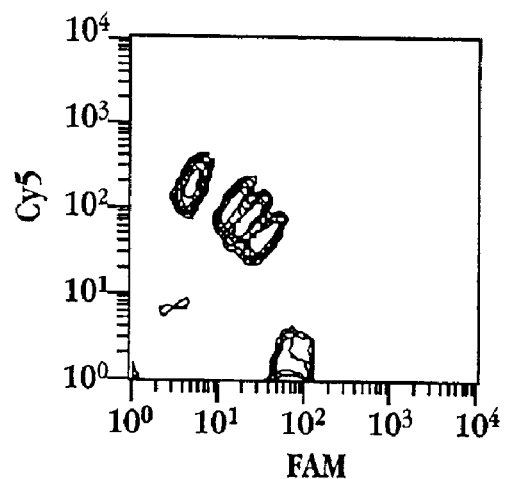

Probe-ratio based FACS (e.g. conventional method, using labeled probes without SID sequences) was run on the model system for comparison. This method was effective in separating a 3:1 ratio hybridized bead population from the 1:1 ratio hybridized bead population in the model system with populations of equal numbers of beads. However, a bead population with a 2:1 ratio of probes was not well resolved from the 1:1 ratio probe population using the conventional method (FIGS. 6C, 7A). See also FIGS. 11A–E, which show data from comparative Example 3, in which a similar model system was analyzed by non-SRQ probe ratio FACS.

SRQ based FACS, using labeled probes with labeled SID sequences, was effective in separating a 2:1 ratio hybridized bead population from the 1:1 ratio hybridized bead population. (FIGS. 6B and 7B; multiply labeled decoders were used for FIG. 6C). However, bead populations with 1.4:1 and 1.2:1 ratios of probes were not always well resolved from the 1:1 ratio probe population (FIGS. 5B and 8B), unless multiply labeled decoders were used (FIG. 5C).

When unlabeled probes were used with labeled SID decoder molecules, beads with probe molar differences as low as 1.4:1 and 1.2:1 could be clearly detected and sorted from beads with a probe molar ratio of 1:1. (FIGS. 4B and 8D; multiply labeled decoders were used for FIG. 4C).

Figure 7C:
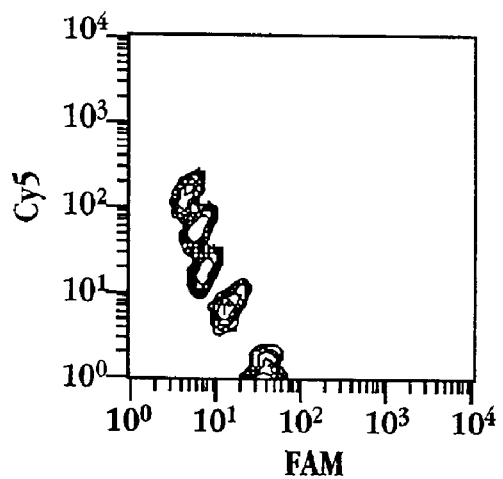
Figure 7D:
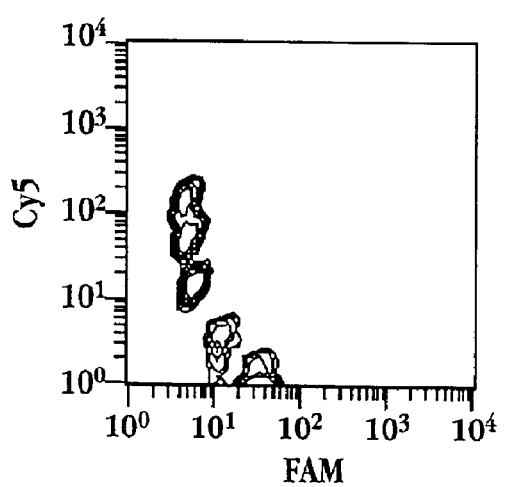
Figure 8A:
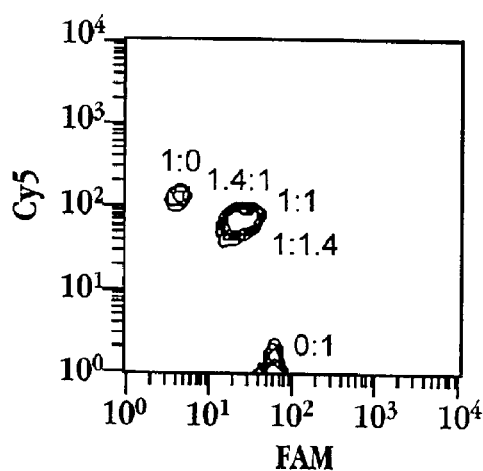
FIGS. 8A–D show FACS sorting data as for FIGS. 7A–D, but where the beads have a 1.4:1 ratio of probes from different sample populations.
Figure 8B:
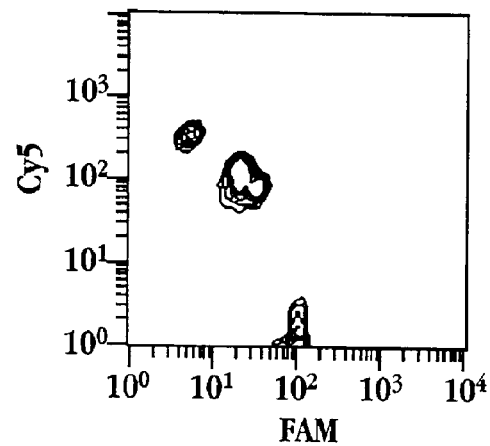
Figure 8C:
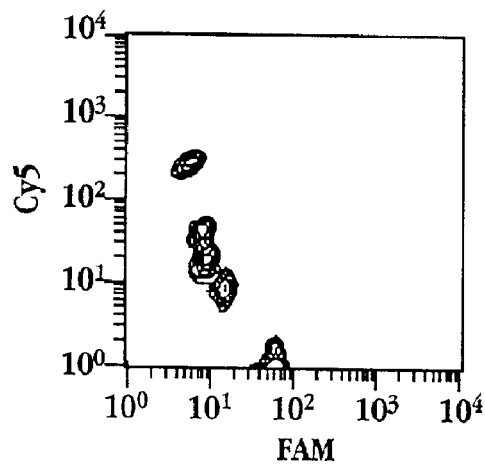
Figure 8D:
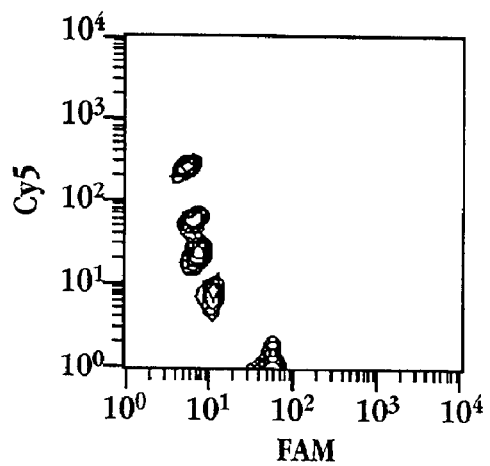

SRQ based FACS with partially labeled probes showed results similar to those obtained with unlabeled probes and multiply labeled decoders for beads with probe ratios close to 1:1 (FIG. 8c), but showed somewhat better resolution than the unlabeled probe system at higher probe ratios (FIG. 7C).

VI. Identification of Sorted Genes

Sorted genes of interest may be identified in parallel by MPSS, which is a combination of two techniques: one for tagging and sorting fragments of DNA for parallel processing (e.g. Brenner et al., CT Pubn. No. WO 9641011), as described above, and another for the stepwise sequencing the end of a DNA fragment (e.g. Brenner, U.S. Pat. No. 5,599,675 and Albrecht et al., PCT Pubn. No. WO 9746704).

This stepwise sequencing method is preferably carried out with the following steps:

(a) ligating an encoded adaptor to an end of a fragment, the encoded adaptor having a nuclease recognition site of a nuclease whose cleavage site is separate from its recognition site; (b) identifying one or more nucleotides at the end of the fragment by the identity of the encoded adaptor ligated thereto; (c) cleaving the fragment with a nuclease recognizing the nuclease recognition site of the encoded adaptor such that the fragment is shortened by one or more nucleotides; and (d) repeating said steps (a) through (c) until said nucleotide sequence of the end of the fragment is determined.

The encoded adaptors each have a protruding strand and an oligonucleotide tag selected from a minimally cross-hybridizing set of oligonucleotides, as taught by Albrecht et al., PCT Pubn. No. WO 9746704. Encoded adaptors whose protruding strands form perfectly matched duplexes with the complementary protruding strands of a fragment are ligated. After ligation, the identity and ordering of the nucleotides in the protruding strand is determined, or "decoded," by specifically hybridizing a labeled tag complement, or "decoder" (not to be confused with the decoder moieties used in the SRQ process), to its corresponding tag on the ligated adaptor. In the identification step, successive sets of tag complements, or "de-coders," are specifically hybridized to the respective tags carried by the ligated encoded adaptors. The type and sequence of nucleotides in the protruding strands of the polynucleotides are identified by the label carried by the specifically hybridized de-coder and the set from which the de-coder came, as described in U.S. Pat. No. 5,599,675.

Figure 12A:
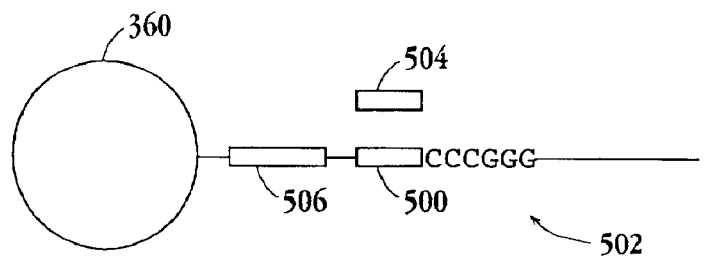
FIGS. 12A–B illustrates procedures for sequencing DNAs isolated by FACS sorting.

Gene products carried by microparticles may be also identified after sorting, e.g. by FACS, using conventional DNA sequencing protocols. Suitable templates for such sequencing may be generated in several different ways starting from the sorted microparticles carrying differentially represented nucleic acids. For example, the reference DNA attached to an isolated microparticle may be used to generate labeled extension products by cycle sequencing, e.g. as taught by Brenner, PCT Pubn. No. WO 9612039. In this embodiment, primer binding site (500) is engineered into the reference DNA (502) distal to tag complement (506), as shown in FIG. 12A. After isolating a microparticle, e.g. by sorting into separate microtiter well, or the like, the differentially expressed strands are melted off, primer (504) is added, and a conventional Sanger sequencing reaction is carried out so that labeled extension products are formed. These products are then separated by electrophoresis, or like techniques, for sequence determination.

Figure 12B:
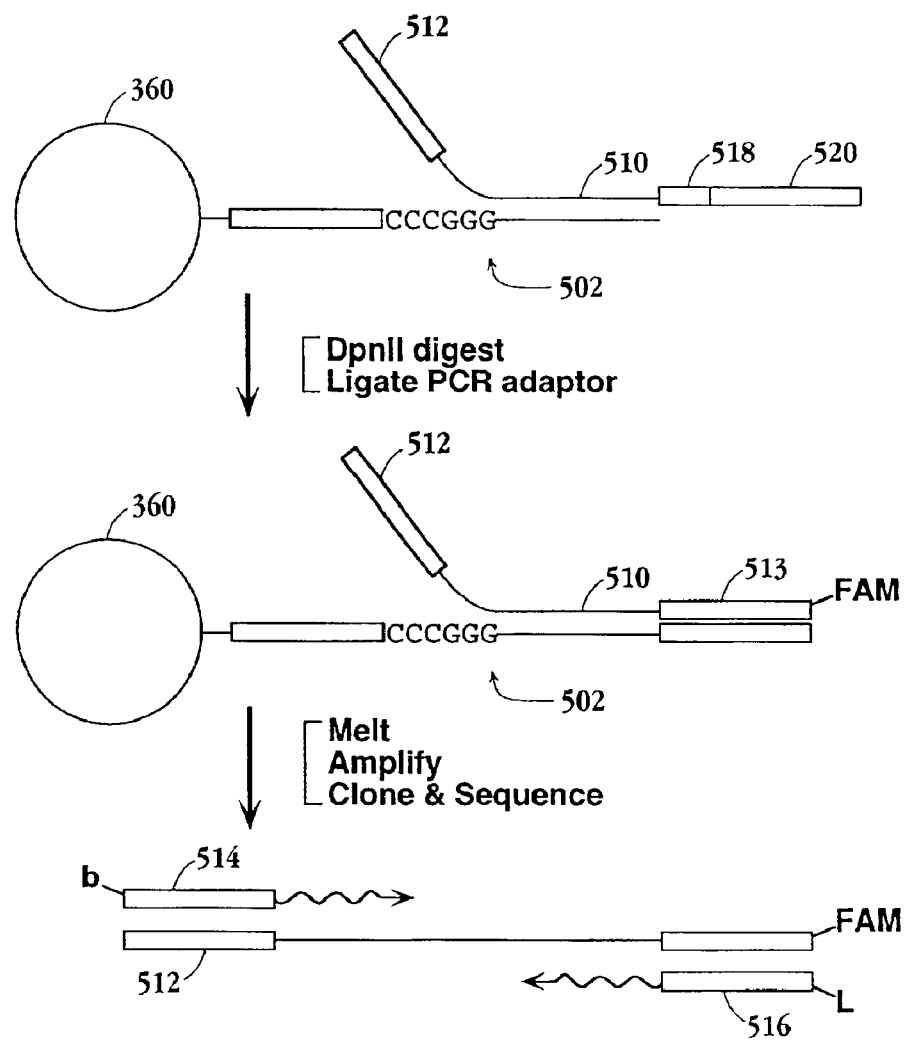

In another embodiment, a primer binding site may be engineered into the competitively hybridized probes (510), at the terminus distal to the SID tag sequences. This primer binding site (512) need not have a complementary strand in the reference DNA (502). After sorting, the sorted beads may be digested with a restriction enzyme, e.g. DpnII here, to remove the SID and decoder sequences ((518) and (520)), and a further primer binding site may be ligated via an adapter (522) to the free end of the reference DNA/probe duplex. (See FIG. 12B.) The probes are then melted off of the reference DNA and amplified by PCR, using primers (514) and (516). The melted and amplified strands are then cloned into a conventional sequencing vector, such as M13, which is used to transfect a host which, in turn, is plated. Individual colonies are picked for sequencing.

EXAMPLES

The following examples illustrate but are not intended to limit the invention.

Mathematical Analysis of DNA fluid Array FACS

Log scaled plots are used in FACS to accommodate the large range of fluorescence signals being measured. It is assumed that DNA probe strands labeled with a single fluorescence dye do not quench each other when hybridized onto the same bead. It is also assumed that the fluorescent dyes used to label decoders are of the same or similar color as those used to label the corresponding probes, and, therefore, the intensities of two fluorescence signals are both linear proportional to the number of the corresponding probes being hybridized onto the beads and to the number of decoders added to the remainders.

The standard deviation of a particular FACS data distribution was estimated from the real dot plot data by measuring the half of width of a rectangular area covering 68% of events from the whole cross area of the bead population.

Gate setting: The boundaries between desired bead populations and the background beads can be represented by lines parallel to the 1:1 probe ratio in a log scale graph of fluorescence ratios. Distances between boundaries (lines) are generally determined by the regression lines and the relative sizes of the populations to achieve balanced high yield and high purity sorting.

Example 1

Construction of a cDNA Reference Library on Microparticles by the Use of Oligonucleotide Tags In this example, a preferred protocol for preparing tagged reference DNA for loading onto microparticles is described. Briefly, cDNA from each of the cell or tissue types of interest is prepared and directionally cloned into a vector containing the tag element of Formula I. Preferably, the mRNA extracted from such cells or tissues is combined, usually in equal proportions, prior to first strand synthesis. mRNA is obtained using standard protocols, after which first and second strand synthesis is carried out as exemplified and the resulting cDNAs are inserted into a vector containing a tag element of Formula I, or like tag element. The vectors containing the tag-cDNA conjugates are then used to transform a suitable host, typically a conventional bacterial host, after which a sample of cells from the host culture is further expanded and vector DNA is extracted. The tag-cDNA conjugates are preferably amplified from the vectors by PCR and processed as described below for loading onto microparticles derivatized with tag complements. After the non-covalently attached strand is melted off, the cDNA-containing microparticles are ready to accept competitively hybridized gene products. Specific guidance relating to the indicated steps is available in Sambrook et al. (cited above); Ausbel et al., editors, Current Protocols in Molecular Biology (John Wiley & Sons, New York, 1995); and like guides on molecular biology techniques.

A pellet of approximately 5 µg of mRNA is resuspended in 45 µl (final volume) of a first strand pre-mix consisting of 10 µl 5 ×SuperScript buffer (250 mM Tris-Cl, pH 8.3, 375 mM KCl, and 15 mM MgCl2) (GIBCO/BRL) (or like reverse transcriptase buffer), 5 µl 0.1 M dithiothreitol (DTT), 2.5 µl 3dNTP/methyl-dCTP mix (10 µM each of dATP, dGTP, dTTP, and 5-methyl-dCTP, e.g available from Pharmacia Biotech), 1 µl RNasin, 12 µl 0.25 µg/µl of reverse transcription primer shown below, and 14.5 µl water.

5'-biotin-GACATGCCTYCATTGAGACGATTCTTTTTTTTTTTTTTV
        Reverse Transcription Primer (SEQ ID NO:10)

After incubation for 15 min at room temperature, 5 ml of 200 U/µL SuperScript is added and the mixture is incubated for 1 hr at 42° C. After the 1 hr incubation, the above mixture (about 50 µl total) is added to a second-strand premix on ice (volume 336 µL) consisting of 80 µl 5×second-strand buffer (94 mM Tris-Cl, pH 6.9, 453 mM KCl, 23 MM MgCl$_2$, and 50 mM (NH$_4$)2SO$_4$ to give a total reaction volume of about 386 µl. Separately, 4 µl of 0.8 U/µl RNase H (3.2 units) and 10 µl of 10 unit/µl E. coli DNA polymerase I (100 units) are combined, and the combined enzyme mixture is added to the above second-strand reaction mixture, after which the total reaction volume is microfuged 5 sec and then incubated for 1 hr at 16° C. and for 1 hr at room temperature to give the following double stranded cDNA (SEQ ID NO:11):

```
5'-biotin-
GACATGCTGCATTGAGACGATTCTTTTTTTTTTTTTTTTVXXX...XGATCXXX-3'
CTGTACGACGTAACTCTGCTAAGAAAAAAAAAAAAAAAAABXXX...XCTAGXXX-5'
          ↑                                    ↑
        Bsm BI                               Dpn II
``` where the X's indicated nucleotides in the cDNAs, V represents A, C, or G, and B represents C, G, or T. Note that the reverse transcription primer sequence has been selected to give a Bsm BI site in the cDNAs which results in a 5'-GCAT overhang upon digestion with Bsm BI.

After phenol/chloroform extraction and ethanol precipitation, the cDNA is resuspended in the manufacturer's recommended buffer for digestion with Dpn II (New England Biolabs, Beverly, Mass.), which is followed by capture of the biotinylated fragment on avidinated beads (Dynal, Oslo, Norway). After washing, the captured fragments are digested with Bsm BI to release the following cDNAs (SEQ ID NOs:12 and 13) which are precipitated in ethanol:

```
GCATTGAGACGATTCTTTTTTTTTTTTTTTTVXXX...X      -3'

ACTCTGCTAAGAAAAAAAAAAAAAAAAAABXXX...XCTAG -5'
```

A conventional cloning vector, such as BlueScript II, pBC, or the like (Stratagene Cloning Systems, La Jolla, Calif.), is engineered to have the following sequence of elements (SEQ ID NO:14) (which are similar to those shown in Formula I, SEQ ID NO: 1):

```
5'-..TTAATTAAGGA [TAG] GGGCCCGCATAAGTCTTC [STUFFER] GGATCC..-3'

3'-..AATTAATTCCT [TAG] CCCGGGCGTATTCAGAAG [STUFFER] CCTAGG..-5'
        ↑                        ↑                    ↑
      Pac I                    Bbs I                Bam HI
```

After digestion with Bbs I and Bam HI, the vector is purified by gel electrophoresis and combined with the cDNAs for ligation. Note that the vector has been engineered so that the Bbs I digestion results in an end compatible with the Bsm BI-digested end of the cDNAs. After ligation, a suitable host bacteria is transformed and a culture is expanded for subsequent use.

From the expanded culture, a sample of host cells are plated to determine the fraction that carry vectors with inserted cDNAs, after which an aliquot of culture corresponding to about 1.7×105 insert-containing cells is withdrawn and separately expanded in culture. This represents about one percent of the repertoire of tags of the type illustrated in Formula I.

Preferably, the tag-cDNA conjugates are amplified out of the vectors by PCR using a conventional protocol, such as the following. For each of 8 replicate PCRs, the following reaction components are combined: 1 µl vector DNA (125 ng/µl for a library, $10^9$ copies for a single clone); 10 µl 10×Klentaq Buffer (Clontech Laboratories, Palo Alto, Calif.); 0.25 µl biotinylated 20-mer "forward" PCR primer (1 nmol/µl); 0.25 µl FAM-labeled 20-mer "reverse" PCR primer (1 nmol/µl); 1 µl 25 mM dATP, dGTP, dTTP, and 5-methyl-dCTP (total dNTP concentration 100 mM); 5 µl DMSO; 2 µl 50× Klentaq enzye; and 80.5 µl water (for a total volume of 100 µl). The PCR is run in an MJR DNA Engine (MJ Research), or like thermal cycler, with the following protocol: 1) 94° C. for 4 min; 2) 94° C. 30 sec; 3) 67° C. 3 min; 4) 8 cycles of step 2 and 3; 5) 94° C. 30 sec, 6) 64° C. 3 min, 7) 22 cycles of steps 5 and 6; 8) 67° C. for 3 min; and 9) hold at 40° C.

The 8 PCR mixtures are pooled and 700 µl phenol is added at room temperature, after which the combined mixture is vortexed for 20–30 sec and then centrifuged at high speed (e.g. 14,000 rpm in an Eppendorf bench top centrifuge, or like instrument) for 3 min. The supernatant is removed and combined with 700 µl chloroform (24:1 mixture of chloroform:iso-amyl alcohol) in a new tube, vortexed for 20–30 sec, and centrifuged for 1 min, after which the supernatant is transferred to a new tube and combined with 80 µl 3M sodium acetate and 580 µl isopropanol. After centrifuging for 20 min, the supernatant is removed and 1 ml 70% ethanol is added. The mixture is centrifuged for 5–10 min, after which the ethanol is removed and the precipitated DNA is dried in a speedvac.

After resuspension, the cDNA is purified on avidinated magnetic beads (Dynal) using the manufacturer's recommended protocol and digested with Pac I (1 unit of enzyme per µg of DNA), also using the manufacturer's recommended protocol (New England Biolabs, Beverly, Mass.) The cleaved DNA is extracted with phenol/chloroform followed by ethanol precipitation. The tags of the tag-cDNA conjugates are rendered single stranded by combining 2 units of T4 DNA polymerase (New England Biolabs) per fg of streptavidin-purified DNA. 150 µg of streptavidin-purified DNA is resuspended in 200 µl water and combined with the following reaction components: 30 µl 10 NEB Buffer No. 2 (New England Biolabs); 9 µl 100 mM dGTP; 30 µl T4 DNA polymerase (10 units/µL); and 31 µL water; to give a final reaction volume of 300 µl. After incubation for 1 hr at 37° C., the reaction is stopped by adding 20 µl 0.5 M EDTA, and the T4 DNA polymerase is inactivated by incubating the reaction mixture for 20 min at 75° C. The tag-cDNA conjugates are puified by phenol/chloroform extraction and ethanol precipitation.

5 µm GMA beads with tag complements are prepared by combinatorial synthesis on an automated DNA synthesizer (Gene Assembler Special /4 Primers, Pharmacia Biotech, Bjorkgatan, Sweden, or like instument) using conventional phosphoramidite chemistry, wherein nucleotides are condenced in the 3'→5' direction. In a preferred embodiment, a 28-nucleotide "spacer" sequence is synthesized, followed by the tag complement sequence (8 "words" of 4 nucleotides each for a total of 32 nucleotides in the tag complement), and a sequence of three C's. Thus, the beads are devivatized with a 63-mer oligonucleotide. The length of the "spacer" sequence is not critical; however, the proximity of the bead surface may affect the activity of enzymes that are use to treat tag complements or captured sequences. Therefore, if such processing is employed, a spacer long enough to avoid such surface effects is desirable. Preferably, the spacer is between 10 and 30 nucleotides, inclusive. The following sequence (SEQ ID NO:15), containing a Pac I site, is employed in the present embodiment:

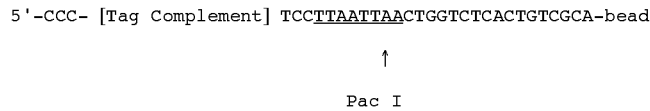

Preferably, the tag-cDNA conjugates are hybridized to tag compliments on beads of a number corresponding to at least a full repertoire of tag complements, which in the case of the present embodiment is $8^8$ or about $1.6 \times 10^7$ beads. The number of beads in a given volume is readily estimated with a hemocytometer.

Prior to hybridization of the tag-cDNA conjugates, the 5' ends of the tag complements are phosphorylated, preferably by treatment with a polynucleotide kinase. Briefly, $2.5 \times 10^8$ beads suspended in 100 µl water are combined with 100 µl 10×NEB buffer No. 2 (New England Biolabs, Beverly, Mass.), 10 µl 100 mM ATP, 1 µl 10% Tween 20, 17 µl T4 polynucleotide kinase (10 units/µl), and 772 µl water for a final volume of 1000 µl. After incubating for 2 hr at 37° C. with vortexing, the temperature is increased to 65° C. for 20 min to inactivate the kinase, with continued vortexing. After incubation, the beads are washed twice by spinning down the beads and resuspending them in 1 ml TE (Sambrook et al., Molecular Cloning, Second Edition, Cold Spring Harbor Laboratory) containing 0.01% Tween 20.

For hybridization of tag-cDNA conjugates to tag complements, the tag-cDNA conjugates as prepared above are suspended in 50 µl water and the resulting mixture is combined with 40 µl 2.5×hybridization buffer, after which the combined mixture is filtered through a Spin-X spin column (0.22 µn) using a conventional protocol to give a filtrate containing the tag-cDNA conjugates. (5 ml of the 2.5×hybridization buffer consists of 1.25 ml 0.1 M NaPO$_4$ (pH 7.2), 1.25 ml 5 M NaCl, 0.25 ml 0.5% Tween 20, 1.50 ml 25% dextran sulfate, and 0.75 ml water.) Approximately $1.8 \times 10^7$ beads in 10 µl TE/Tween buffer (TE with 0.01% Tween 20) is centrifuged so that the beads form a pellet and the TE/Tween is removed. To the beads, 25 µl of 1×hybridization buffer (10 mM NaPO$_4$ (pH 7.2), 500 mM NaCl, 0.01% Tween 20, 3% dextran sulfate) is added and the mixture is vortexed to fully resuspend the beads, after which the mixture is centrifuged so that the beads form a pellet and the supernatant is removed.

The tag-cDNA conjugates in the above filtrate are incubated at 75° C. for 3 min and combined with the beads, after which the mixture is vortexed to fully resuspend the beads. The resulting mixture is further incubated at 75° C. with vortexing for approximately three days (60 hours). After hybridization, the mixture is centrifuged for 2 min and the supernatant is removed, after which the beads are washed twice with 500 µil TE/Tween and resuspended in 500 µl 1×NEB buffer No. 2 with 0.01% Tween 20. The beads are incubated at 64° degree C. in this solution for 30 min., after which the mixture is centrifuged so that the beads form a pellet, the supernatant is removed, and the beads are resuspended in 500 µl TE/Tween.

Loaded beads are sorted from unloaded beads using a high speed cell sorter, preferably a MoFlo flow cytometer equiped with an argon ion laser operating at 488 nm (Cytomation, Inc., Ft. Collins, Colo.), or like instrument. After sorting, the loaded beads are subjected to a fill-in reaction by combining them with the following reaction components: 10 µl 10×NEB buffer No. 2, 0.4 µl 25 mM dNTPs, 1 µl 1% Tween 20, 2 µl T4 DNA polymerase (10 units/ml), and 86.6 µl water, for a final reaction volume of 100 µl. After incubation at 12° C. for 30 min with vortexing, the reaction mixture is centrifuged so that the beads form a pellet and the supernatant is removed. The pelleted beads are resuspended in a ligation buffer consisting of 15 µl 10×NEB buffer No. 2, 1.5 µl 1% Tween 20, 1.5 µl 100 mM ATP, 1 µl T4 DNA ligase (400 units/ ml), and 131 µl water, to give a final volume of 150 µl. The ligation reaction mixture is incubated at 37° C. for 1 hr with vortexing, after which the beads are pelleted and washed once with 1×phosphate buffered saline (PBS) with 1 mM CaCl$_2$. The beads are resuspended in 45 µl PBS (with 1 mM CaCl$_2$) and combined with 6 µl Pronase solution (10 mg/ml, Boehringer Mannheim, Indianapolis, Ind.), after which the mixture is incubated at 37° C. for 1 hr with vortexing. After centrifugation, the loaded beads are washed twice with TE/Tween and then once with 1×NEB Dpn II buffer (New England Biolabs, Beverly, Mass.).

he tag-cDNA conjugates loaded onto beads are cleaved with Dpn II to produce a four-nucleotide protruding strand to which a complementary adaptor carying a 3'-label is ligated. Accordingly, the loaded beads are added to a reaction mixture consisting of the following components: 10 µl 10×NEB Dpn II buffer, 1 µl 1% Tween, 4 µl Dpn II (50 units/ml), and 85 µl water, to give a final reaction volume of 100 µl. The mixture is incubated at 37C. overnight with vortexing, after which the beads are pelleted, the supernatant is removed, and the beads are washed once with 1×NEB buffer No. 3. To prevent self-ligation, the protruding strands of the tag-cDNA conjugates are treated with a phosphatase, e.g. calf intestine phosphatase (CIP), to remove the 5' phosphates. Accordingly, the loaded beads are added to a reaction mixture consisting of the following components: 10 µl 10×NEB buffer No. 3, 1 µl 1% Tween 20, 5 µl CIP (10 units/µl), and 84 µl water, to give a final reaction volume of 100 µl. The resulting mixture is incubated at 37° C. for 1 hr with vortexing, after which the beads are pelleted, washed once in PBS containing 1 mM CaCl$_2$, treated with Pronase as described above, washed twice with TE/Tween, and once with 1×NEB buffer No. 2.

The following 3'-labeled adaptor (SEQ ID NOs:16 and 17) is prepared using conventional reagents, e.g. Clontech Laboratories (Palo Alto, Calif.):

where "p" is a 5' phosphate group and "FAM" is a fluorescein dye attached to the 3' carbon of the last nucleotide of the top strand by a commercially available 3' linker group (Clontech Laboratories). The ligation is carried out in the following reaction mixture: 5 µl 10×NEB buffer No. 2, 0.5 µl 1% Tween 20, 0.5 µl 100 mM ATP, 5 ml 3'-labeled adaptor (100 pmol/µl ), 2.5 µl T4 DNA ligase (400 units/A) and 36.5 µl water, to give a final reaction volume of 50 µl. The reaction mixture is incubated at 16° C. overnight with vortexing, after which the beads are washed once with PBS containing 1 mM CaC2 and treated with Pronase as described above. After this initial ligation, the nick remaining between the adaptor and tag-cDNA conjugate is sealed by simultaneously treating with both a kinase and a ligase as follows. Loaded beads are resuspended in a reaction mixture consisting of the following components: 15 μl 10×NEB buffer No. 2, 1.5 μl 1% Tween 20, 1.5 μl 100 mM ATP, 2 μl T4 polynucleotide kinase (10 units/μl), 1 μl T4 DNA ligase (400 units/μl), and 129 μl water, for a final reaction volume of 150 μl. The reaction mixture is incubated at 37° C. for 1 hr with vortexing, after which the beads are washed once with PBS containing 1 mM $CaCl_2$, treated with Pronase as described above, and washed twice with TE/Tween.

After the labeled strand is melted off, preferably by treatment with 150 mM NaOH, the reference DNA on the beads is ready for competitive hybridization of differentially expressed gene products.

Example 2

Preparation of a Yeast Reference DNA Population Attached to Microparticles

In this example, *Saccharomyces cerevisiae* cells of strain YJM920 MATa Gal+SUC2 CUP1 are grown in separate rich and minimal media cultures essentially as describe by Wodicka et al. (cited above). mRNA extracted from cells grown under both conditions are used to establish a reference cDNA population which is tagged, sampled, amplified, labeled, and loaded onto microparticles. Loaded microparticles are isolated by FACS, labels are removed, and the non-covalently bound strands of the loaded DNA are melted off and removed.

Yeast cells are grown at 30° C. either in rich medium consisting of YPD (yeast extract/peptone/glucose, Bufferad, Newark, N.J.) or in minimal medium (yeast nitrogen base without amino acids, plus glucose, Bufferad). Cell density is measured by counting cells from duplicate dilutions, and the number of viable cells per milliliter is estimated by plating dilutions of the cultures on YPD agar immediately before collecting cells for mRNA extraction. Cells is mid-log phase ($1.5 \times 10^7$ cells/ml) are pelleted, washed twice with AE buffer solution (50 mM NaAc, pH 5.2, 10 mM EDTA), frozen in a dry ice-ethanol bath, and stored at −80° C.

mRNA is extracted as follows for both the construction of the reference DNA library and for preparation of DNA for competitive hybridization. Total RNA is extracted from frozen cell pellets using a hot phenol method, described by Schmitt et al., *Nucleic Acids Research* 18:3091–3092 (1990), with the addition of a chloroform-isoamyl alcohol extraction just before precipitation of the total RNA. Phase-Lock Gel (5 Prime-3 Prime, Inc., Boulder, Colo.) is used for all organic extractions to increase RNA recovery and decrease the potential for contamination of the RNA with material from the organic interface. Poly(A)+ RNA is purified from the total RNA with an oligo-dT selection step (Oligotex, Qiagen, Chatsworth, Calif.).

5 μl each of mRNA from cells grown on rich medium and minimal medium are mixed for construction of a cDNA library in a pUC19 containing the tag repertoire of Formula I. The tag repertoire of Formula I is digested with Eco RI and Bam HI and inserted into a similarly digested pUC19. The mRNA is reverse transcribed with a commercially available kit (Strategene, La Jolla, Calif.) using an olgio-dT primer containing a sequence which generates a Bsm BI site identical to that of Formula I upon second strand synthesis. The resulting cDNAs are cleaved with Bsm BI and Dpn II and inserted into the tag-containing pUC19 after digestion with Bsm BI and Bamr HI. After transfection and colony formation, the density of pUC19 tranformants is determined so that a sample containing approximately thirty thousand tag-cDNA conjugates may be obtained and expanded in culture. Alternatively, a sample of tag-cDNA conjugates are obtained by picking approximately 30 thousand clones, which are then mixed and expanded in culture.

From a standard miniprep of plasmid, the tag-cDNA conjugates are amplified by PCR with 5-methyldeoxycytosine triphosphate substituted for deoxycytosine triphosphate. The following 19-mer forward and reverse primers (SEQ ID NO:18 and SEQ ID NO:19), specific for flanking sequences in pUC19, are used in the reaction:

```
forward primer:
5'-biotin-AGTGAATTCGGGCCTTAATTAA reverse primer:
5'-FAM-GTACCCGCGGCCGCGGTCGACTCTAGAGGATC
``` where "FAM" is an NHS ester of fluorescein (Clontech Laboratories, Palo Alto, Calif.) coupled to the 5' end of the reverse primer via an amino linkage, e.g. Aminolinker 11 (Perkin-Elmer, Applied Biosystems Division, Foster City, Calif.). The reverse primer is selected so that a Not I site is reconstituted in the double stranded product. After PCR amplification, the tag-cDNA conjugates are isolated on avidinated beads, e.g. M-280 Dynabeads (Dynal, Oslo, Norway).

After washing, the cDNAs bound to the beads are digested with Pac I releasing the tag-cDNA conjugates and a stripping reaction is carried out to render the oligonucleotide tags single stranded. After the reaction is quenched, the tag-cDNA conjugate is purified by phenol-chloroform extraction and combined with 5.5 μm GMA beads carrying tag complements, each tag complement having a 5' phosphate. Hybridization is conducted under stringent conditions in the presence of a thermal stable ligase so that only tags forming perfectly matched duplexes with their complements are ligated. The GMA beads are washed and the loaded beads are concentrated by FACS sorting, using the fluorescently labelled cDNAs to identify loaded GMA beads. The isolated beads are treated with Pac I to remove the fluorescent label, after which the beads are heated in an NaOH solution using conventional protocols to remove the non-covalently bound strand. After several washes the GMA beads are ready for competitive hybridization.

Example 3

FACS Analysis of Microparticles Loaded with Different Ratios of DNAs Labeled with Fluorescein and CY5: Comparative Example In this example, the sensitivity of detecting different ratios of differently labeled cDNAs by non-SRQ probe ratio methods was evaluated by constructing a reference DNA population consisting of a single clone and competitively hybridizing to the reference DNA population different ratios of complementary strands labeled with different fluorescent dyes. The reference DNA population consisted of a cDNA clone, designated "88.11," which is an 87-basepair fragment of an expressed gene of the human monocyte cell line THP-1, available from the American Type Culture Collection (Rockville, Md.) under accession number TIB 202. The nucleotide sequence of 88.11 has a high degree of homology to many entries in the GenBank Expressed Sequence Tag library, e.g. GB AA830602 (98%). The reference DNA population, which consisted of only 88.11 cDNA, was prepared as described in Example 1, with the exception that a special population of microparticles was prepared in which all microparticles had the same tag complement attached. The corresponding oligonucleotide tag was attached to the 88.11 cDNA. Thus, only monospecific populations of tags and tag complements were involved in the experiment. After competitive hybridization, the loaded microparticles were analyzed on a Cytomation, Inc. (Ft. Collins, Colo.) FACS instrument as described above.

88.11 cDNA was also cloned into a vector identical to that of Example 1 (330 of FIG. 3B), except that it did not contain tag 336. 10 μg of vector DNA was linearized by cleaving to completion with Sau 3A, an isoschizomer of Dpn II (342 of FIG. 3B), after which two 1 μg aliquots of the purified linear DNA were taken. From each 1 μg aliquot, about 20 μg of labeled single stranded DNA product was produced by repeated cycles of linear amplification using primers specific for primer binding site 332. In one aliquot, product was labeled by incorporation of rhodamine R110 labeled dUTP (PE Applied Biosystems, Foster City, Calif.); and in the other aliquot, product was labeled by incorporation of CY5-labeled dUTP (Amersham Corporation, Arlington Heights, Ill.). Quantities of the labeled products were combined to form seven 5 μg amounts of the two products in ratios of 1:1, 2:1, 1:2, 4:1, 1:4, 8:1, and 1:8. The 5 μg quantities of labeled product were seperately hybridized to $1.6 \times 10^5$ microparticles (GMA beads with 88.11 cDNA attached) overnight at 65C. in 50 μ4×SSC with 0.2% SDS, after which the reaction was quenched by diluting to 10 ml with ice-cold TE/Tween buffer (defined above). The loaded microparticles were centrifuged, washed by suspending in 0.5 ml 1×SSC with 0.2% SDS for 15 min at 65C., centrifuged, and washed again by suspending in 0.5 ml 0.1×SSC with 0.2% SDS for 15 min at 55C. After the second washing, the microparticles were centrifuged and resuspended in 0.5 ml TE/Tween solution for FACS analysis.

Figure 11A:
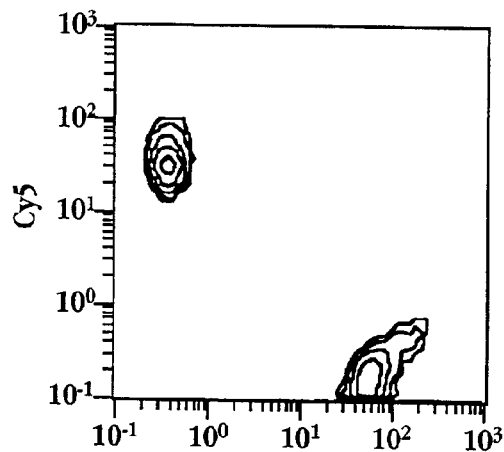
FIGS. 11A–E illustrate flow analysis data of microparticles carrying predetermined ratios of two differently labeled cDNAs, using non-SRQ competitive hybridization analysis, as described in Example 3.
Figure 11B:
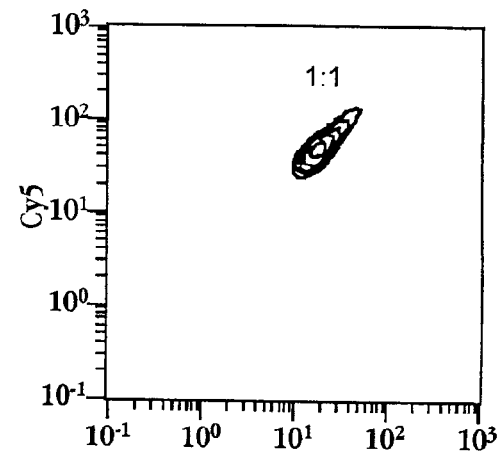
Figure 11C:
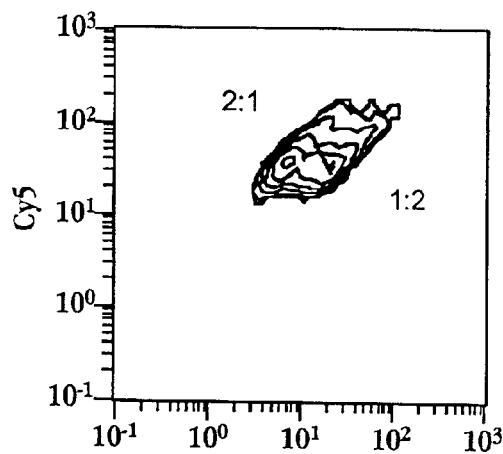
Figure 11D:
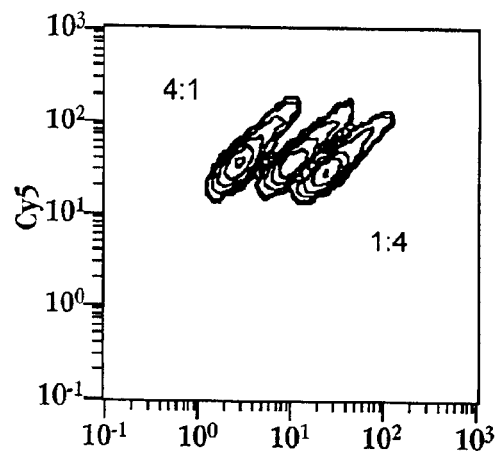
Figure 11E:
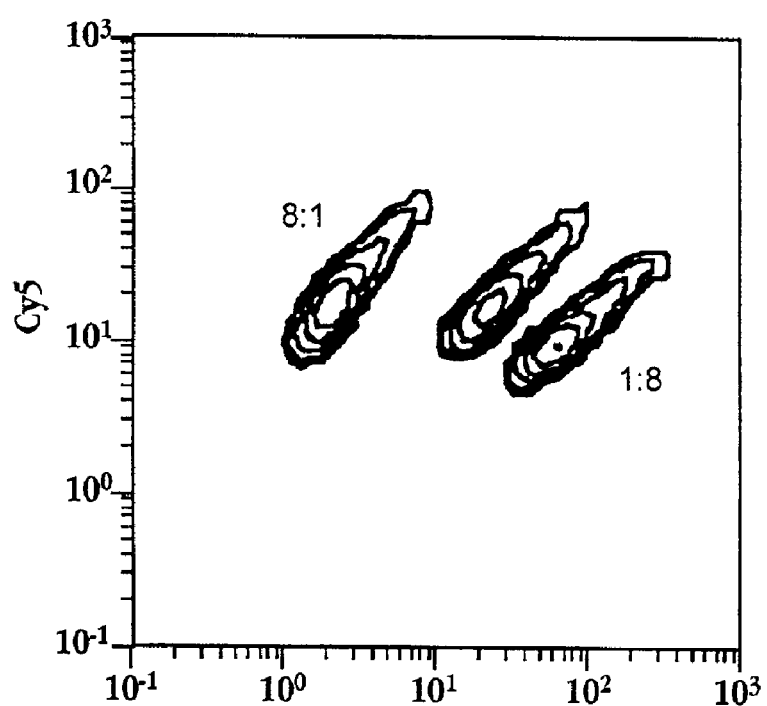

The results are shown in FIGS. 11A–E, where in each Figure the vertical axis corresponds to CY5 fluorescence and the horizontal axis corresponds to rhodamine R110 fluorescence. In FIG. 5A, a population of microparticles were combined that had either all R110-labeled DNA or all CY5-labeled DNA hybridized to the complementary reference strands. Contours 550 and 552 are clearly distinguished by the detection system of the FACS instrument and microparticles of both populations produce readily detectable signals. FIG. 11B illustrates the case where the R110- and CY5-labeled strands are hybridized in equal proportions. As expected, the resulting contour is located on the diagonal of the graph and corresponds to the position expected for non-regulated genes. FIGS. 11C through 11E show the analysis of three pairs of competitive hybridizations: i) R110- and CY5-labeled strands hybridized in a 2:1 concentration ratio and a 1:2 concentration ratio, ii) R110- and CY5-labeled strands hybridized in a 4:1 concentration ratio and a 1:4 concentration ratio, and iii) R110- and CY5-labeled strands hybridized in an 8:1 concentration ratio and a 1:8 concentration ratio.

The data of FIG. 11C suggest that genes up-regulated or down-regulated by a factor of two or more are detectable by non-SRQ FACS sorting, but that significant overlap may exist between signals generated by regulated and non-regulated genes, especially at lower ratios. FIGS. 11D and 11E suggest that genes up-regulated or down-regulated by a factor of four or higher are readily detectable over non-regulated genes by this method.

Example 4

FACS Analysis of Differentially Expressed Genes from Stimulated and Unstimulated THP-1 Cells In this example, a reference DNA population attached to microparticles was constructed from cDNA derived from THP-1 cells stimulated as indicated below. Equal concentrations of labeled cDNAs from both stimulated (by treatment with phorbol 12-myristate 13-acetate (PMA) and lipopolysaccharide (LPS)) and unstimulated THP-1 cells were then competitively hybridized to the reference DNA population, as described in Example 1, and the microparticles carrying the labeled cDNAs were analyzed by a FACS instrument, using non-SRQ probe ratio methods.

THP-1 cells were grown in T-165 flasks (Costar, No. 3151) containing 50 ml DMEM/F12 media (Gibco, No. 11320–033) supplemented with 10% fetal bovine serum (FBS)(Gibco, No. 26140–038), 100 units/mi penicillin, 100 μg/ml streptomycin (Gibco, No. 15140–122), and 0.5 μMI β-mercapto ethanol (Sigma, No. M3148). Cultures were seeded with $1 \times 10^5$ cells/ml and grown to a maximal density of 1106. Doubling time of the cell populations in culture was about 36 hours. Cells were treated with PMA as follows: Cells from a flask (about $5 \times 10^7$ cells) were centrifuged (Beckman model GS-6R) at 1200 rpm for 5 minutes and resuspended in 50 ml of fresh culture media (without antibiotics) containing 5 μd of 1.0 mM PMA (Sigma, No. P-8139) in DMSO (Gibco No. 21985023) or 5 μl A DMSO (for the unstimulated population), after which the cells were cultured for 48 hours. Following the 48 hour incubation, media and non-adherent cells were aspirated from the experimental flask (i.e. containing stimulated cells) and fresh media (without antibiotics) was added, the fresh media containing 10 μl of 5 mg/ml LPS (Sigma, No. L-4130) in phosphate buffered saline (PBS). The culture of unstimulated cells was centrifuiged (Beckman model GS-6R) at 1200 rpm for 5 minutes at 4° C. so that a pellet formed which was then resuspended in 50 ml of fresh growth media containing 10 μl PBS. Both the cultures of stimulated and unstimulated cells were incubated at 37° C. for four hours, after which cells were harvested as follows: Media was aspirated from the cultures and adherent cells were washed twice with warm PBS, after which 10 ml PBS was added and the cells were dislodged with a cell scaper. The dislodged cells were collected and their concentration was determined with a hemocytometer, after which they were centrifuged (Beckman model GS-6R) at 1200 rpm for 5 minutes to form a pellet which was used immediately for RNA extraction.

MRNA was extracted from about $5 \times 10^6$ cells using a FastTrack 2.0 kit (No. K1593–02, Invitrogen, Inc. San Diego, Calif.) for isolating mRNA. The manufacturer's protocol was followed without significant alterations. A reference DNA population attached to microparticles was constructed from mRNA extracted from stimulated cells, as described in Example 1. Separate cDNA libaries were constructed from mRNA extracted from stimulated and unstimulated cells. The vectors used for the libraries were identical to that of Example 1, except that they did not contain oligonucleotide tags (336 of FIG. 3B). Following the protocol of Example 3, approximately 2.5 μg of rhodamine R110-labeled single stranded DNA was produced from the cDNA library derived from stimulated cells, and approximately 2.5 μg of CY5-labeled single stranded DNA was produced from the cDNA library derived from unstimulated cells. The two 2.5 μg aliquots were mixed and competitively hybridized to the reference DNA on $9.34 \times 10^5$ microparticles. The reaction conditions and protocol was as described in Example 3.

Figure 13:
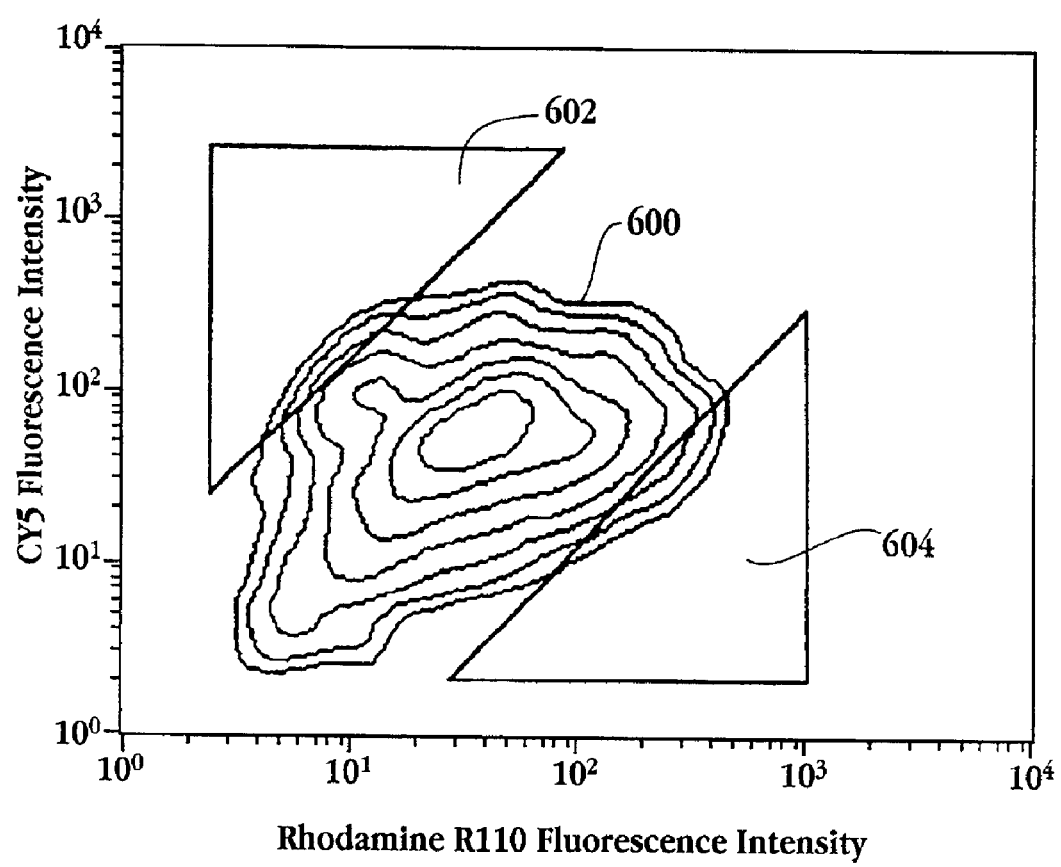
FIG. 13 illustrates flow analysis data of microparticles carrying differently labeled cDNAs from stimulated and unstimulated THP-1 cells.

After hybridization, the microparticles were sorted by a Cytomation, Inc. MoFlo FACS instrument using non-SRQ labeled probes. FIG. 13 contains a conventional FACS contour plot 600 of the frequencies of microparticles with different fluorescent intensity values for the two fluorescent dyes. Approximately 10,000 microparticles corresponding to up-regulated genes (sort window 602 of FIG. 13) were isolated, and approximately 12,000 microparticles corresponding to down-regulated genes (sort window 604 of FIG. 13) were isolated. After melting off the labeled strands, as described above, the cDNAs carried by the microparticles were amplified using a commericial PCR cloning kit (Clontech Laboratories, Palo Alto, Calif.), and cloned into the manufacturer's recommended cloning vector. After transformation, expansion of a host culture, and plating, 87 colonies of up-regulated cDNAs were picked and 73 colonies of down-regulated cDNAs were picked. cDNAs carried by plasmids extracted from these colonies were sequenced entional protocols on a PE Applied Biosystems model 373 automated DNA. The identified sequences are listed in Tables 1 and 2.

TABLE 1

Up-Regulated Genes

| No. Copies | Description | GenBank Identifier |
|---|---|---|
| 19 | LD78/MIP-1 | HUMCKLD78 |
| 16 | TNF-inducible (TSF-6) mRNA | HUMTSG6A |
| 15 | GRO-γ (MIP-2β) | HUMGROG5 |
| 6 | GRO-β. (MIP-2α) | HUMGROB |
| 6 | act-2 | HUMACT2A |
| 4 | guanylate binding protein isoform I (GBP-2) | HUMGBP1 |
| 4 | spermidine/spermine N1-acetyltransferase | HUMSPERMNA |
| 4 | adipocyte lipid-binding protein | HUMALBP |
| 3 | fibronectin | HSFIB1 |
| 3 | interleukin-8 | HSMDNCF |
| 1 | insulin-like growth factor binding protein 3 | HSIGFBP3M |
| 1 | interferon-γ inducible early response gene | HSINFGER |
| 1 | type IV collagenase | |
| 1 | cathepsin L | HSCATHL |
| 1 | EST | |
| 1 | EST | |
| 1 | genomic/EST | HSAC002079 |

TABLE 2

Down-Regulated Genes

| No. Copies | Description | GenBank Identifier |
|---|---|---|
| 16 | elongation factor 1 | HSEF1AC |
| 4 | ribosomal protein S3a/v-fos tranf. effector | HUMFTE1A |
| 6 | ribosomal protein S7 | HUMRPS17 |
| 2 | translationally controlled tumor protein | HSTUMP |
| 3 | 23 kD highly basic protein | HS23KDHBP |
| 2 | laminin receptor | HUMLAMR |
| 2 | cytoskeletal gamma-actin | HSACTCGR |
| 2 | ribosomal protein L6 | HSRPL6AA |
| 2 | ribosomal protein L10 | HUMRP10A |
| 2 | ribosomal protein L21 | HSU14967 |
| 2 | ribosomal protein S27 | HSU57847 |
| 1 | ribosomal protein L5 | HSU14966 |
| 1 | ribosomal protein L9 | HSU09953 |
| 1 | ribosomal protein L17 | HSRPL17 |
| 1 | ribosomal protein L30 | HSRPL30 |
| 1 | ribosomal protein L38 | HSRPL38 |
| 1 | ribosomal protein S8 | HSRPS8 |
| 1 | ribosomal protein S13 | HSRPS13 |
| 1 | ribosomal protein S18 | HSRPS18 |
| 1 | ribosomal protein S20 | HUMRPS20 |
| 1 | acidic ribosomal phosphoprotein PO | HUMPPARP0 |
| 1 | 26S proteasome subunit p97 | HUM26SPSP |
| 1 | DNA-binding protein B | HUMAAE |
| 1 | T-cell cyclophilin | HSCYCR |
| 1 | interferon inducible 6-26 mRNA | HSIFNIN4 |
| 1 | hematopoetic proteoglycan core protein | HSHPCP |

TABLE 2-continued

Down-Regulated Genes

| No. Copies | Description | GenBank Identifier |
|---|---|---|
| 1 | fau | HSFAU |
| 1 | β-actin | HSACTB |
| 1 | nuclear enc. mito. serine hydroxymethyltrans. | HUMSHMTB |
| 1 | mito. cytochrome c oxidase subunit II | HUMMTCDK |
| 1 | genomic | W92931 |
| 1 | EST | W84529 |
| 1 | EST | AA933890 |
| 1 | EST | AA206288 |
| 1 | EST | AA649735 |
| 1 | EST | N34678 |
| 1 | EST | AA166702 |
| 1 | EST | AA630799 |
| 3 | genomic | AA630797 |

Example 5

High Resolution FACS Sorting of Microbead-Supported DNA Clones via Probe Subtraction Remainder Quantification (SRQ)

A. Preparation of Monobead Reference Library

The model system used a monobead reference library, i.e. a microbead library of a single monoclonal DNA sequence of 176 bp from the human Y-chromosome (TTY2.1, see reference above). Beads were loaded with DNA (the above sequence plus a the 28 mer spacer and 32 mer 8-word tag sequence) at 1.2 μg per $1 \times 10^6$ beads, using loading procedures as described herein in Sections I and II, and in references cited therein. The monobeads were cut with 150 units of DpnII per $0.5 \sim 1 \times 10^6$ beads in 100 μl 1×DpnII buffer with 0.01% Tween at 37° C. for 16 hr to remove the free end PCR adaptor sequence. A single DpnII digestion gave a yield of about 92%, and additional DpnII digestion gave a 96% yield. The DpnII digested beads were treated with 0.15 N sodium hydroxide to strip off the non-covalent-binding DNA strand, giving beads having 3' attached ssDNAs with a 5'-Pi-GATC sequence.

B. Preparation of SID Tagged Probes

The probes were prepared to have additional 3'-end tag sequences of either -GAG or -CTC, representing two different probe sample sources (M and F, respectively), so that upon hybridization to the target DNA on the beads the different probe will generate two different overhang 3'-ends which are complementary to each other but not to themselves.

The above-referenced TTY2.1 plasmid clone was modified with an insert of either MQ or FQ adaptor, as shown below, containing the tag (bold) and an EarI site sequence (underlined), at the DpnII site adjacent to the Y-DNA insert.

```
MQ-adaptor
5'pATCGAGAGAAGAGCGTGCACAGGAA              (SEQ ID NO:4)
     CTCTCTTCTCGCACGTGTCCTT-5'            (SEQ ID NO:5)

5'Biotin-TTCCTGTGCACGCTCTTCT - PCR primer (SEQ ID NO:6)

FQ-adaptor
5'pATCCTCAGAAGAGCGTGCACTCCGA              (SEQ ID NO:7)
     GAGTCTTCTCGCACGTGAGGCT-5'            (SEQ ID NO:8)

5'Biotin-TCGGAGTGCACGCTCTTCT - PCR primer (SEQ ID NO:9)
```

Both constructs were then amplified by PCR and purified with the Qiaquick PCR Kit. (For complex probes, 5-methyl-dCTP is used in the PCR to protect the DNA from EarI cleavage in later steps. The PCR products were then digested with EarI (100 units EarI per 20 µg DNA in 100–150 µL NEB1 buffer, 37° C. for 16h) and end repaired with dNTPs using Klenow DNA polymerase (20 units Klenow per 20 µg DNA and 33 µM dNTPs in 200 µL, 75° C. for 15 min) to generate the full length, SID tagged double stranded DNA probes. The reaction was then heated at 25° C. for 10 min to inactivate the enzyme. Residual uncut DNA was removed through Biotin affinity purification. Single stranded DNA probes were prepared using λ exonuclease (50 units per 20 µg ds DNA at 37° C. for 30 min, 75° C. for 10 min).

Fluorescently labeled probes were prepared by using either Cy5 (for M probe, with GAG-3' tag) or FAM (for F probe, with CTC-3' tag) labeled 5'-end primers. These labeled probes were used for regular probe-ratio based FACS analysis, and for probe-ratio plus subtraction-remainder quantification based FACS analysis.

C. Competitive Hybridization of Probes with Microbeads

The monoclonal TTY-DNA microbeads were hybridized with the two probes according to procedures described herein and in Brenner et al., *PNAS* 97(4):1665–70 (2000). Specifically, 20,000 beads were mixed with a total of 200 ng dsDNA probes, or 100 ng ssDNA probes, in 100 µl of bead hybridization buffer (4×SSC, 0.1% SDS and 25% formamide), heated to 90° C. for 3 min, and then incubated at 65° C. for 16 hr with constant mixing.

In separate experiments, aliquots of 20,000 microbeads each were hybridized separately with two tagged probes (fluorescently labeled or unlabeled) mixed at ratios, i.e. 1:2 and 2:1 test ratios, 1:1 ratio reference control, 1:0 and 0:1 maxim/null signal controls.

After hybridization, the microbeads were washed once with 1 ml of ice-cold TE/Tween buffer, once with 1×SSC/0.1% SDS at 65° C. for 30 min, and once with 0.1×SSC/0.1% SDS at 65° C. for 30 min, to remove non-specifically bound probes from the beads. The beads were finally washed twice with 1 ml TE/Tween, and all the beads from the five separate hybridizations described above were combined into a micro-tube for attachment of decoder molecules and FACS analysis.

D. SID Tag Annealing and Attachment of Probe SID Tag Decoders

As described above, hybridization of the tagged probes to the target DNA strand on the beads produces 3'-end overhang sequences of the first SID and second SID sequences, which, under appropriate conditions, are able to anneal to each other (intra-bead) in a 1 to 1 ratio. The remainder, or unhybridized first SID or second SID sequences, represents the molar excess of the probe from the corresponding sample source, and can be identified qualitatively and quantitatively with a pair of fluorescently labeled SID tag reporter (or decoder) molecules.

The probe SID decoders used in this system, shown below, were a Cy5 labeled adaptor with a CTC-3' overhang and a FAM labeled adaptor with a GAG-3' overhang, for the M probe and F probe, respectively.

```
M-Cy5-decoder
5' AGAAGAGCGTGCACAGGAA                    (SEQ ID NO: 20)

CTCTCTTCTCGCACGTGTCCTT-peg-peg-Cy5-5'    (SEQ ID NO: 21)

F-FAM-decoder
5' AGAAGAGCGTGCACTCCGA                    (SEQ ID NO: 22)

GAGTCTTCTCGCACGTGAGGCT-peg-peg-FAM-5'    (SEQ ID NO: 23)
```

The probe-hybridized microbeads were incubated with T4 DNA ligase and the two tag-decoders, under conditions which facilitate intrabead ligation between the two types of SID tags and between each remainder and its corresponding decoders, e.g., at low bead concentration of beads and high decoder concentration. An aliquot of 20,000 beads was washed into 96 µl of NEB/Tween buffer. Then, 1 µl of 100 mM ATP and 1 µl of T4 DNA ligase (2000 U/µl) were added to the suspended microbeads, and the ligation mixture was immediately incubated at 16° C. with constant mixing, to prevent precipitation of beads and inter-bead ligation. Immediately or after 1 to 3 minutes, 2 µl of the fluorescent SID-decoder mixture (5 µM each) was added. The ligation reaction was carried out for 1 to 2 hours at 16° C. with constant mixing.

The ligase was then inactivated by addition of 1 ml of 1×SSC/0.1% SDS (preheated to 65° C.) and incubation at 65° C. with constant mixing for 10 to 15 min. The beads were then spun down and washed twice in 1 ml of 0.1× SSC/0.1% SDS at room temperature, to remove non-ligated decoder from the beads. The beads were finally washed twice with 1 ml TE/Tween buffer.

E. FACS Analysis

FACS analysis was performed with the FACScalibur (Becton Dickinson). Settings were adjusted to approximately equalize the Cy5 signal from the Cy5-probe-only array beads and the FAM signal from the FAM-probe only array beads. For each five-ratio array experiment, 2000 to 2500 beads were gated from the FSC-height/SSC-height acquisition plot for the Cy5/FAM fluorescence analysis in the F14-height/F11-height plot. The results are discussed above in Section V.D and illustrated in FIGS. 4–8.

Example 7

Preparation of SRQ Probes from Genomic DNA

This protocol, illustrated in FIGS. 9A–B, describes a representative procedure for generating SID tagged probes from two genomic DNA samples A and B for SRQ competitive hybridization assays.

a) Sau3A/Mbo1 Digestion and dGTP fill-in

For each of the two DNA samples, 5 $\mu$g was dissolved to a volume of 40 $\mu$L water in 0.2ml PCR tubes. To each tube was added 10 $\mu$L of a GATC digest mix prepared from 11 $\mu$L 10×NEB4 buffer, 1.1 $\mu$l BSA, 4.4 $\mu$l 25U/$\mu$l Mbo1, and 5.5 $\mu$l 20U/$\mu$l Sau3A. The mixtures were incubated for 5 hrs at 37° C. and (optionally) heated for 20 min at 60° C. to inactivate the enzymes. To each mixture was then added 10 $\mu$L of a fill-in mix prepared from 2.3 $\mu$l 10×NEB4 buffer, 2.3 $\mu$l 2 mM dGTP, 16.1 $\mu$l H2O and 2.3 $\mu$l Klenow (exo-) 5U/$\mu$L. The mixtures were incubated for 30 min at 37° C., followed by 20 min at 75° C. 20 min to inactivate the enzymes.

b) Ligation to Q adaptors

To 0.8 $\mu$g of each filled-in DNA digest in 10 $\mu$L water was added 1.5 $\mu$L 10 mM Q adaptor (different adaptors for A and B samples), 1 $\mu$l 10×NEB4, 2 $\mu$l 10 mM ATP, 1 $\mu$l T4 DNA ligase (400U), and 4.5 $\mu$l H2O. The mixtures are incubated at 16° C. overnight, then at 65° C. for 10 min to inactivate the ligase.

c) PCR Amplification of Q—Q Fragments

To each ligation sample, above, was added 99.5 $\mu$L of a PCR mix prepared from 86 $\mu$L water, 10 $\mu$L 10×HSTaq buffer, 1 $\mu$L 25 mM dNTP, 2 $\mu$L primer, and 0.5 $\mu$L HSTaq polymerase. PCR was run for 22 cycles (94° C. 30"55° C. 30", 72° C. 60"). The samples were purified on a Qiagen mini column, using Quiquick Gel buffer, according to the manufacturer's protocol.

As noted above, PCR amplification of unlabled probes may be carried out in a single mixture.

At this point, UV spectra may be taken to calculate the DNA purity and concentration. The yield of 2 PCRs is generally about 5 $\mu$g.

d) Digestion with Sbf1 and Dephosphorylation

To each purified Q-Q PCR sample (2 $\mu$g) in 0.2-ml tubes was added 5 $\mu$l 10×SE-Y buffer, 3 $\mu$t Sbf1 (5U/$\mu$l), and water to 42 $\mu$L. The mixture was incubated at 37 ° C. for 5 hrs or overnight. For dephosphorylation, 1 $\mu$l Shrimp alkaline phosphatase (1 U/$\mu$l) was added to 48 $\mu$l of each Sbf1 digested DNA sample, and the mixture was incubated at 37° C. for 30–60 min, and at 65° C. for 20 min. The mixture was purified using the Qiaquick Gel Extraction Kit essentially as described in step (c) above.

e) Ligation to S-adaptor

To 15 $\mu$l (~1 $\mu$g) purified Sbf1/SAP DNA from step (d) was added 2 $\mu$l 10×ligase buffer, 1 $\mu$l 10$\mu$M S-adaptor, and 2 $\mu$l T4 DNA ligase (400U/$\mu$l); the mixture was incubated at 16° C. overnight, then at 65° C. for 10 min.

f) Exonuclease III Digestion

To 15 $\mu$t S-adaptor ligated DNA from step (f) above was added 15 $\mu$l 50 mM Tris-Cl (pH 7.5) and 0.51 $\mu$l ExoIII (200U/$\mu$l); the mixture was incubated at 37° C. for 2 hrs, then at 75° C. for 10 min.

g) PCR with S and Q Primers

To 0.5$\mu$l of template DNA (~1.5 $\mu$g) was added a PCR mix prepared from 86$\mu$L water, 10 $\mu$L 10×HSTaq buffer, 1 $\mu$L 25 mM dNTP, 1 $\mu$L 100 $\mu$M Q primer, 1 $\mu$l 100$\mu$M S primer, and 0.5 $\mu$L HSTaq polymerase. PCR was run essentially as described for step c) above, using 5-MeCTP to protect internal Ear1 sites from digestion in the next step.

The amplification is purified using the Qiaquick PCR kit, essentially as described above, to inactivate the DNA polymerase and remove primers and dNTPs.

As noted above, PCR amplification of unlabled probes may be carried out in a single mixture.

At this point, UV spectra may be taken to calculate the DNA purity and concentration. The yield of 4 PCRs is generally about 7~10 $\mu$g.

h) Ear 1 Digestion of Double Stranded Probes

This digestion generates 5'-phosphoryl ends for the subsequent exonuclease digestion, and retains on the probes the different SID tags on the different Q adaptors used in step (b) above.

To 6~10 $\mu$g double stranded probe DNA was added 60~100U Ear1, 10 $\mu$L 10×NEB1 buffer, and water to 100 $\mu$L. The mixture was incubated at 37° C. 5 hr to overnight, then at 65° C. for 20 min to inactivate the enzyme.

i) λ Exonuclease Digestion

The samples were first precipitated as follows. Equal amounts of ds probes (2.5~5 $\mu$g each), e.g. 50 $\mu$L each, were transferred into 0.5 mL tubes, and ⅒ volume of 3M NaOAc was added, followed by 2 volumes of 100% ethanol, vortexing to mix after each addition. The mixtures were cooled at −70° C. for >10 min and spun at 1400 rpm for 15 min; the supernatant was removed, followed by addition of 0.5 ml 70% ethanol, spining at 1400 rpm for 10 min, and removal of supernatant.

The samples were air dried and dissolved in 16 $\mu$l water, and to each was added 2 $\mu$l 10×λ exonuclease buffer and 2 $\mu$l λ exonuclease (10U/$\mu$l). The mixture was incubated for 30–60 min at 37° C., then for 10 min at 95° C., to denature any ds structure. The single stranded probes are stored in ice water or at −20° C. for longer term storage.

While the invention has been described with reference to specific methods and embodiments, it will be appreciated that various modifications may be made without departing from the invention.

It is claimed:

1. A method for determining the relative abundance of a nucleic acid sequence between first and second nucleic acid populations, comprising:

(a) contacting a reference library which comprises multiple copies of a selected nucleic acid sequence with:

a first probe, derived from a first nucleic acid population, having a sequence which is complementary to said selected sequence and a terminal first sample ID (SID) sequence, and a second probe, derived from a second nucleic acid population, having a sequence which is complementary to said selected sequence and a terminal second sample ID (SID) sequence;

wherein said first and second probes are present in relative amounts proportional to the relative abundance of the selected nucleic acid sequence in the first and second nucleic acid populations, respectively, whereby, upon said contacting, (i) said first and second probes competitively hybridize with said selected sequence in said reference library, such that;

the ratio of duplexes formed by the first probe with said selected sequence to duplexes formed by the second probe with said selected sequence is proportional to the ratio of the amount of the selected sequence in the first nucleic acid population to the amount of the selected sequence in the second nucleic acid population, and said first and second SID sequences are present as single stranded extensions on said duplexes; and (ii) said first SID sequences on said duplexes formed by the first probe with said selected sequence and said second SID sequences on said duplexes formed by the second probe with said selected sequence hybridize with each other in a 1:1 ratio; and further comprising (b) detecting the presence of unhybridized first SID sequences and/or unhybridized second SID sequences, as an indication of the relative amounts of hybridized first probe and hybridized second probe.

2. The method of claim 1, wherein in said contacting step (a), a plurality of different-sequence probes derived from said first nucleic acid population, each having said first SID sequence, and a plurality of different-sequence probes derived from said second nucleic acid population, each having said second SID sequence, are contacted with said reference library, said reference library comprises multiple copies of different sequences which are complementary to the different sequences present in the first and second nucleic acid populations, and different sequences within the library are attached to spatially distinct solid phase supports in clonal subpopulations.

3. The method of claim 2, wherein said spatially distinct solid phase supports are separate regions of a planar support.

4. The method of claim 2, wherein said spatially distinct solid phase supports are microparticles.

5. The method of claim 2, wherein said detecting comprises attaching a labeled first or second decoder moiety to each said unhybridized first or second SID sequence.

6. The method of claim 5, wherein a first light-generating label is present on first decoder moieties selectively attachable to unhybridized first SID sequences, and a second, distinguishable light-generating label is present on second decoder moieties selectively attachable to unhybridized second SID sequences.

7. The method of claim 6, wherein each said decoder moiety includes a terminal oligonucleotide sequence that is complementary to either said first or said second SID sequence.

8. The method of claim 5, wherein said first or second labeled decoder moiety is a fluorescent dye molecule.

9. The method of claim 5, wherein said first or second labeled decoder moiety comprises multiple fluorescent dye molecules.

10. The method of claim 8, wherein said spatially distinct solid phase supports are microparticles, and further comprising:

sorting said microparticles by fluoresence-activated flow sorting (FACS) according to the ratio of fluorescent signals generated by said fluorescent dye molecules on each microparticle.

11. The method of claim 10, further comprising:
accumulating in a separate vessel each said microparticle having a value of said ratio of fluorescent signals within one or more selected ranges of values; and
determining a nucleotide sequence of a portion of the nucleic acid sequence on one or more of said microparticles.

12. The method of claim 6, wherein said first and second probes are further labeled with said first and second light-generating labels, respectively.

13. The method of claim 6, wherein a known fraction of said first and second probes are further labeled with said first and second light-generating labels, respectively.

14. The method of claim 1, wherein said first and second SID sequences are complementary and thus hybridize with each other directly.

15. The method of claim 1, wherein said first and second SID sequences hybridize with each other through an intermediate molecule comprising sequences complementary to said first and second SID sequences, and wherein the method further comprises, concurrent with or following step (a), contacting said intermediate molecule with said reference library and first and second probes.

16. The method of claim 2, for use in analysis of differentially regulated or expressed genes, wherein said first and second nucleic acid populations are cDNA libraries derived from expressed genes from a plurality of sources selected from different cells, tissues, or individuals; and said reference DNA library is derived from genes expressed in the plurality of different sources.

17. The method of claim 2, for use in analysis of genetic variations among different individuals or different populations of individuals, wherein said first and second nucleic acid populations are genomic DNA libraries derived from different individuals or, different populations of individuals and said reference DNA library is derived from pooled genomic DNA of said different individuals or different populations of individuals.

18. A method for sorting a population of nucleic acid sequences in accordance with their relative abundance in first and second nucleic acid populations, comprising:
(a) providing a reference library which comprises the nucleic acid sequences present in the first and second nucleic acid populations, wherein said nucleic acid sequences are attached to microparticles, such that different sequences within the library are attached to different microparticles in clonal subpopulations;
(b) contacting said reference library with a plurality of first probes derived from said first nucleic acid population, each probe having a sequence which is complementary to a reference library sequence and a terminal first sample ID (SID) sequence, and a plurality of second probes derived from said second nucleic acid population, each probe having a sequence which is complementary to a reference library sequence and a terminal second sample ID (SID) sequence,
wherein said first and second probes having the same sequence, exclusive of the first and second SID sequences, are present in relative amounts proportional to the relative abundance of the complement of said same sequence in the first and second nucleic acid populations, respectively,
and whereby, upon said contacting,
(i) said first and second probes competitively hybridize with complementary sequences attached to said microparticles in said reference library, thereby forming duplexes, such that:
the ratio of said duplexes formed by the first probe to duplexes formed by the second probe having the same sequences, exclusive of the first and second SID sequences, is proportional to the ratio of the amount of the complement of said same sequence in the first nucleic acid population to the amount of the complement of said same sequence in the second nucleic acid population, and
said first and second SID sequences are present as single stranded extensions on said duplexes; and
(ii) said first SID sequences on said duplexes and said second SID sequences on said duplexes hybridize with each other in a 1:1 ratio;
(c) applying to each first SID sequence which is not hybridized in (ii), a first decoder moiety having a first fluorescent label, wherein said first decoder moieties are selectively attachable to unhybridized first SID sequences, and applying to each second SID sequence which is not hybridized in (ii), a second decoder moiety having a second, distinguishable fluorescent label, wherein said second decoder moieties are selectively attachable to unhybridized second SID sequences; and
(d) sorting said microparticles by fluorescence-activated flow sorting (FACS) according to the ratio of fluorescent signals generated by the fluorescent labels on each microparticle.

19. The method of claim 18, wherein said first decoder moiety includes a terminal oligonucleotide sequence that is complementary to said first SID sequence, and said second decoder moiety includes a terminal oligonucleotide sequence that is complementary to said second SID sequence.

20. The method of claim 19, wherein said first or second decoder moiety comprises multiple fluorescent molecules.

* * * * *